US011207413B2

(12) United States Patent
Speaker et al.

(10) Patent No.: US 11,207,413 B2
(45) Date of Patent: Dec. 28, 2021

(54) SUCCULENT EXTRACT AND ALGINATE COMBINED SOLUTIONS AND PRODUCTS INCORPORATING THEM

(71) Applicant: Capsulent, Santa Cruz, CA (US)

(72) Inventors: Tycho Joseph Speaker, Santa Cruz, CA (US); W. Preston Brawn, Bradenton, FL (US)

(73) Assignee: Capsulent, Santa Cruz, CA (US)

( * ) Notice: Subject to any disclaimer, the term of this patent is extended or adjusted under 35 U.S.C. 154(b) by 690 days.

(21) Appl. No.: 15/565,702

(22) PCT Filed: Apr. 12, 2016

(86) PCT No.: PCT/US2016/027098
§ 371 (c)(1),
(2) Date: Oct. 11, 2017

(87) PCT Pub. No.: WO2016/168179
PCT Pub. Date: Oct. 20, 2016

(65) Prior Publication Data
US 2018/0078648 A1 Mar. 22, 2018

Related U.S. Application Data

(60) Provisional application No. 62/146,603, filed on Apr. 13, 2015.

(51) Int. Cl.
| | | |
|---|---|---|
| *A61K 36/00* | (2006.01) |
| *A61K 47/46* | (2006.01) |
| *A61K 47/36* | (2006.01) |
| *A61K 36/886* | (2006.01) |
| *A61K 36/36* | (2006.01) |
| *A61K 9/10* | (2006.01) |
| *A61K 36/88* | (2006.01) |
| *A61K 9/107* | (2006.01) |
| *A61K 47/26* | (2006.01) |
| *A61K 36/41* | (2006.01) |
| *A23L 33/105* | (2016.01) |
| *A23L 33/16* | (2016.01) |
| *A23L 33/125* | (2016.01) |
| *A61K 8/9794* | (2017.01) |
| *A61K 8/9789* | (2017.01) |
| *A23L 2/52* | (2006.01) |
| *A61K 8/73* | (2006.01) |
| *A61K 9/00* | (2006.01) |
| *A61K 9/06* | (2006.01) |
| *A61K 9/14* | (2006.01) |
| *A61K 31/192* | (2006.01) |
| *A61Q 5/00* | (2006.01) |
| *A61Q 19/00* | (2006.01) |
| *C11D 1/66* | (2006.01) |
| *C11D 3/22* | (2006.01) |

(52) U.S. Cl.
CPC ............... *A61K 47/46* (2013.01); *A23L 2/52* (2013.01); *A23L 33/105* (2016.08); *A23L 33/125* (2016.08); *A23L 33/16* (2016.08); *A61K 8/733* (2013.01); *A61K 8/9789* (2017.08); *A61K 8/9794* (2017.08); *A61K 9/0014* (2013.01); *A61K 9/0043* (2013.01); *A61K 9/06* (2013.01); *A61K 9/10* (2013.01); *A61K 9/107* (2013.01); *A61K 9/14* (2013.01); *A61K 31/192* (2013.01); *A61K 36/36* (2013.01); *A61K 36/41* (2013.01); *A61K 36/88* (2013.01); *A61K 36/886* (2013.01); *A61K 47/26* (2013.01); *A61K 47/36* (2013.01); *A61Q 5/00* (2013.01); *A61Q 19/00* (2013.01); *C11D 1/662* (2013.01); *C11D 3/222* (2013.01); *A23V 2002/00* (2013.01)

(58) Field of Classification Search
None
See application file for complete search history.

(56) References Cited

U.S. PATENT DOCUMENTS

| 4,851,224 | A | * | 7/1989 | McAnalley | ............ A61P 37/08 424/744 |
| 2002/0119941 | A1 | | 8/2002 | Ni et al. | |
| 2004/0161435 | A1 | * | 8/2004 | Gupta | .................... A61Q 19/00 424/401 |
| 2006/0105000 | A1 | * | 5/2006 | Friedman | ............. A61K 9/0031 424/400 |
| 2006/0141046 | A1 | * | 6/2006 | Cattaneo | .............. A61K 9/1652 424/489 |
| 2014/0127297 | A1 | * | 5/2014 | Didden | .................. A23K 10/30 424/474 |

FOREIGN PATENT DOCUMENTS

| KR | 20040106108 A | | 12/2004 |
| KR | 2010085411 | * | 7/2010 |

OTHER PUBLICATIONS

Pereira, R., et al., "Alginate/Aloe Vera Hydrogel Films for Biomedical Applications," Jan. 1, 2013, vol. 5, pp. 210-215, XP055510299, Procedia CIRP.

Pereira, R., et al., "Degradation Behavior of Biopolymer-based Membranes for Skin Tissue Regeneration," Jun. 5, 2013, vol. 59, pp. 285-291, XP028563003, Procedia Engineering, Elsevier, Amsterdam, NL.

Pereira, R., et al., "Development of Novel Alginate based Hydrogel Films for Wound Healing Applications," Jan. 1, 2013, vol. 52, pp. 221-230, XP055510599, International Journal of Biological Macromolecules.

(Continued)

*Primary Examiner* — Qiuwen Mi
(74) *Attorney, Agent, or Firm* — RatnerPrestia

(57) ABSTRACT

The invention provides a composition including a succulent extract and an alginic acid component consisting of alginic acid and/or one or more salts thereof, wherein the succulent extract is present in an amount in a range from 0.1 wt % to 1000 wt % relative to the alginic acid component, both on a dry basis.

18 Claims, No Drawings

(56) References Cited

OTHER PUBLICATIONS

Pan, H., et al., "Assessment of the Physical, Mechanical, and Moisture-Retention Properties of Pullulan-Based Ternary Co-Blended Films," May 27, 2014, vol. 112, pp. 94-101, XP029045555, Carbohydrate Polymers, Applied Science Publishers.
Extended European Search Report for European Application No. 16 780 555.5, dated Oct. 8, 2018, 9 pages.
International Search Report and Written Opinion for International Application No. PCT/US2016/027098, dated Jul. 26, 2016—7 Pages.
McConaughy et al., "Tailoring the Network Properties of Ca2+ Crosslinked Aloe Vera Polysaccharide Hydrogels for In Situ Release of Therapeutic Agents", Biomacromolecules, 2008, vol. 9, pp. 3277-3287.
International Preliminary Report on Patentability and Written Opinion for International Application No. PCT/US2016/027098, dated Oct. 17, 2017, 6 pages.
Partial English translation of Mexican Office Action for Mexican Application No. MX/a/2017/013213, dated Nov. 9, 2021, 4 pages.

\* cited by examiner

SUCCULENT EXTRACT AND ALGINATE COMBINED SOLUTIONS AND PRODUCTS INCORPORATING THEM

This application is the National Phase filing of International Patent Application No. PCT/US2016/027098, filed 12 Apr. 2016, and is related to, and claims the benefit of priority of, U.S. Provisional Application No. 62/146,603, entitled SUCCULENT EXTRACT AND ALGINATE COMBINED SOLUTIONS AND PRODUCTS INCORPORATING THEM, filed on 13 Apr. 2015, the contents of which are incorporated herein by reference in their entirety for all purposes.

FIELD OF THE INVENTION

This invention relates generally to the rheological characteristics of liquids, including shear-thinning systems and systems designed to prevent settling or creaming of suspended droplets or particles and to related products and processes for making and using such products. The invention further relates to manufacture of rheologically useful aqueous systems by providing a system wherein synergistic interaction between two components produces more extreme rheological behavior than does either component alone, including rheological thickening, thixotropy, pseudoplastic behavior and gelation. Because the rheology thus achieved is dependent upon this interaction, such products and processes may also be referred to as rheologically synergistic liquid systems and synergistic rheology processes.

BACKGROUND OF THE INVENTION

The use of aqueous polymer solutions as carrier compositions is well known in various arts including pharmaceutical, medical, agricultural, and in the manufacture of a variety of consumer products including those for personal care, home care, foods, beverages, industrial, and many other categories. Liquids of various viscosities may be used for a variety of specific purposes, for example to provide uniform distribution of a material or to provide metered dispensing of a suspended or dissolved active component during use. In particular, liquid systems that exhibit pseudoplastic or "shear-thinning" behavior play important roles in providing products that temporarily thin during use, but rapidly return to a viscous, suspension-stabilizing resting state.

Aqueous solutions of polymers may be used to control suspension, viscosity and shear characteristics of liquid products, and a wide array of single and combined polymer solution systems have been characterized and harnessed for this purpose. Such products can further comprise insoluble inclusions, and depending upon the degree of gelation, can also influence the shape and texture of solid or semi-solid products, So-called synergistic polymer interactions involve the interplay of more than one polymer type, and produce rheological behavior that is different from that of solutions of any of the single polymers alone. Solutions of synergistic polymers may show substantial excursions of characteristics, for instance dramatic thickening or even gelation may be induced by combining two polymers in solution, even when solutions of either component dissolved individually at the same concentrations show rheological properties similar to water. This substantial excursion from the behavior of the components can be beneficial in many ways, for instance in reducing the cost of materials required for a formulation, or in rapidly thickening a thin product in-situ by the addition of the second polymer solution. In some cases the rheology of the synergistic system is not reproducible using any known single polymer system.

A wide variety of synergistic systems have been used in many areas of commerce, but frequently these systems are not heat stable and in particular are not stable to cyclic freezing and thawing. For example, locust bean/xanthan gum systems provide useful synergistic thickening, but irreversibly thin after freezing and thawing. Such thermal instability precludes their use in some broad consumer applications, which require stabilizing products against both temperature cycling and intermittent freezing during shipping and storage.

A very widely known gelled polymer system in commercial use is formed by combining sodium alginate and divalent calcium ions. This system is the principal commercial platform for producing gelled polysaccharide beads and hydrocolloid wound dressings. The gels formed by calcium alginate systems are generally firm and characterized by a high degree of cross-linking that prevents shearing of particles into a smooth paste; rather such gels when sheared break into brittle or grainy particles with a gritty or particulate feel upon skin.

Further, calcium ions and other divalent cations are destabilizing and problematic to a wide variety of formulations, interfering with product stability and other characteristics, and commonly ethylene diamine tetraacetic acid is incorporated to chelate free calcium to combat these effects. In addition calcium salts commonly used in producing calcium alginate gels, for instance calcium chloride solutions, frequently pose substantial hazards in manufacture due to irritancy and the risk of acute contact dermatitis. Thus a need exists on the one hand for a commercially viable gel system that is stable to freeze/thaw cycling, and also one that produces a shearable, soft gel amenable to rubbing onto the skin, and on the other hand for a system that requires only safe, non-harsh constitutive components.

SUMMARY OF THE INVENTION

The invention provides a composition including a succulent extract and an alginic acid component consisting of alginic acid and/or one or more salts thereof, wherein the succulent extract is present in an amount in a range from 0.1 wt % to 1000 wt % relative to the alginic acid component, both on a dry basis.

DETAILED DESCRIPTION OF THE INVENTION

The inventors combined *Aloe vera* extracts with a sodium alginate solution with the initial intent of adding a skin benefit quality to the sodium alginate solution base. Unexpectedly, the resulting combined solution rapidly became strikingly much more viscous, and yet highly shear-thinning, while neither single solution exhibited this rheological behavior to such a noticeable degree. The composition may be pseudoplastic and/or thixotropic. At higher concentrations the same components form firm, non-flowable gels. The invention teaches the use of *Aloe vera* extract or other succulent extract as a synergistic thickener and gellant for aqueous solutions of alginic acid and/or its salts. The synergistic system remained clear and showed no evidence of precipitation of any components.

Also very unexpectedly, the rheological properties of the combined solution gave the appearance of being nearly constant over a wide temperature range from near-freezing temperature to fully boiling, although in later experiments it was found that, after heating to around 80° C. or cooler, the system rheology was nearly identical after cooling, while heating above 80° C. was associated with some irreversible thinning. Further the rheological system was apparently unaffected by multiple cycles of freezing and thawing.

Very unexpectedly, in addition to rheological synergy, gelation behavior was observed at higher concentrations, and alginate solutions introduced to *Aloe* solutions gel in a manner similar to that induced by divalent cations. The inventors initially postulated that this might be due to calcium and ions that might be present in succulents, and submitted samples for elemental analysis (Galbraith Laboratories, Knoxville, Tenn.). These results are presented in Table 1, which shows that calcium levels are in fact substantial and potentially sufficient to be used to induce rheological changes in alginate solutions. The inventors further investigated aqueous calcium chloride solutions with calcium at levels comparable to the analyzed *Aloe*, and found gelation and thickening of alginate by such calcium solutions were in many respects similar to the systems formed by *Aloe* (and other succulents described below). However, these systems differed in an important and surprising respect. Particles formed by dropping an alginate solution into a calcium bath form a tough, insoluble skin on the exterior, where calcium ions are understood to cross-link the alginate strongly. Particles formed by the analogous method of the invention, wherein the calcium bath is replaced by an *Aloe* solution of the same calcium concentration, do not form a tough skin. Rather the particles are apparently homogeneous throughout, and are shearable to form a uniform paste with no stringy residue. Without being bound to a particular explanation, it appears that the succulent extract supplies both calcium, which is known to induce gelation, but also at least one additional component that may block or inhibit the dense cross-linking associated with calcium-induced gelation and the resulting tough skin. Juice pressed from freshly harvested *Carpobrotus edulis* or any of a variety of other succulent plants similarly induces gelation of alginate droplets to form solid particles that are absent any tough skin, and under shear stress, as when crushed between the fingers, are reduced to a uniform paste consistency without stringy residue.

TABLE 1

Calcium content of succulent samples by atomic absorption analysis.

| Sample | Ca (ppm) |
|---|---|
| 1% solution Aloe vera powder | 396 |
| Aloe vera pressed fresh leaf juice | 1570 |
| Carpobrotus Edulis pressed fresh leaf juice | 1570 |

Calcium-alginate cross-linked gel systems are well-known across a variety of industries, and are particularly useful in food technology in that they form thermo-irreversible gels, which retain gelled structure at high temperatures, above 100° C. required for cooking. In some applications the toughness that results from high levels of cross-linking accomplished by calcium is considered beneficial, where particle durability is desired. However, tough particles or residues that are difficult to physically disperse are problematic in many applications, for example when products are applied to skin or where these residues might clog an orifice or a dispensing mechanism. In one aspect the present invention provides a means of producing gelled materials that prevents formation of such tough, non-dispersible cross-linked material, and the resulting shear-dispersible gels. In another aspect the invention provides shear-thinning liquid rheological systems suitable as suspending agents.

While the shear-thinning liquid systems of the invention therefore do contain calcium and have some similarity to typical calcium-alginate gels, the inventors noted important differences between the behaviors of these two types of system. To investigate these properties, the inventors combined equal volumes of a 1% alginate (Manucol DH, FMC Health & Nutrition, Philadelphia, Pa.) aqueous solution and a 0.11% aqueous solution of calcium chloride (Sigma-Aldrich, St. Louis, Mo.) producing a 400 ppm calcium solution equivalent to the level found in a 1% *Aloe* solution, which formed a shear-thinning viscous solution. The resulting solution was compared to the inventive product comprising equal volumes of 1% (Manucol DH, Health & Nutrition, Philadelphia, Pa.) aqueous solution and 1% *Aloe vera* powder (Earth Supplied Products, Naples, Fla.) aqueous solution, and these results are tabulated in Table 2. The suspending capacities of the products thus formed were compared by adding 80-mesh quartz sand and 1 mm ceramic beads (Lysing Matrix D Bulk, MP Biomedicals, LLC, Solon, Ohio). The alginate/*Aloe* system suspended the sand but not the beads, whereas the solution of the same calcium content, but lacking the other components in the *Aloe* solution, readily suspended the beads. Without being bound to an interpretation, the solution of calcium alone appeared to form a stronger gel matrix in the alginate solution, while components of the *Aloe* appeared to limit or inhibit the degree of formation of the cross-linked gel. While *Aloe* (and succulents generally) are demonstrated herein to induce gelation, these data show that component(s) of *Aloe* solutions also appear to modulate calcium-induced cross-linking strength as compared to the gelation induced by simple solutions of free calcium ions.

TABLE 2

Suspending capacity of several shear-thinning alginate solutions

| Alginate (ppm) | Ca (ppm) | Aloe (ppm) | Result |
|---|---|---|---|
| 1,000 | 0 | 1,000 | Suspends sand, not 1 mm ceramic beads |
| 1,000 | 400 | | Suspends sand and 1 mm ceramic beads |

The invention further provides products that are stable to freeze/thaw cycling and also to a wide range of temperatures between freezing and above the boiling point, and thus provides improved performance over many common gum solutions used as thickeners and stabilizers, which alter in viscosity when heated, or precipitate upon freezing. The present inventive systems further confer advantage over calcium alginate bead technology in that the gelled particles and beads produced do not possess a tough skin, and are softer than typical calcium alginate gels and in some embodiments readily rubbed to a soothing paste upon skin or passed freely through a spray nozzle or self-foaming dispenser without clogging. In some aspects the invention provides a product with visible droplets or particles in suspension, that is nonetheless readily atomizable with a finger-pump or trigger sprayer and passes easily through a self-foamer.

As *Aloe* is one among many related succulents, the inventors acquired and extracted juice from a variety of other succulent plants, and surprisingly, the synergistic interaction with alginate was universally observed in every fleshy-leafed succulent sample tested from some 50 different plant types, including members of the order Asparagales, family Asparagaceae, sub-family Agave, the order Caryophyllales, family Aizoaceae, and the order Saxifragales, family Crassulaceae. However, outside of these groups, plant juices or extracts did not produce this behavior. For example none of the cactus samples tested produced synergistic rheology with alginate. Cacti tested included common "prickly pear" (order Caryophyllales, family Cactaceae, *Opuntia ficus-indica*) and other Cactaceae types including *Epiphyllum, Schlumbergera, Stenocereus*, and *Trichocereus*, among others. Similarly, the liquid expressed from common non-succulent plants, including a variety of tree leaves, garden vegetables and ornamental plants, did not induce gelation of alginate.

The invention provides compositions and methods using extracts of succulents in combination with alginic acid and/or its salts as a synergistic combination, which can additionally provide useful shear-thinning suspending agents as well as gelled materials, and related uses and products derived therefrom.

Unless otherwise stated, absolute or relative amounts of materials used herein refer to dry weight basis.

Succulent Extract

As used herein, "succulent extract" refers to the components of the plant extracted from it by water. In some succulent species, for example *Aloe*, the extract may include either or both of two substances: gel and latex. *Aloe* gel is the clear, jelly-like substance found in the inner part of the *Aloe* plant leaf. *Aloe* latex comes from just under the plant's skin and is yellow in color. In some embodiments, the extract of *Aloe* or other succulents may be derived from the whole plant or alternatively from a selected anatomical portion of the plant when it is dissolved and/or when the dissolved extract is combined with the alginate.

One exemplary succulent extract is sold commercially as "*Aloe vera* whole leaf extract," a concentrated dry powder that is very potent for inducing gelation of alginate solutions. The clear liquid gel separated from fresh *Aloe* leaves does not gel alginate as strongly unless concentrated, as by evaporation. A strongly gelling substance can also be obtained by simply crushing the skin portion of the fresh plant and filtering the liquid thereby produced. Extracting dry "*Aloe vera* whole leaf extract" powder with 90% ethanol also produces a liquid that will gel alginate. Extraction of the same powder with 80% ethanol produces a more highly active extract in regard to inducing alginate gelation. While useful gelation requires a minimum concentration of the succulent extract material, an extremely dilute extract may still induce gelation in a product that is subsequently concentrated, for example upon drying. The concentrated gel from the interior of the leaf, excluding the outer rind, is sold commercially as "*Aloe vera* inner leaf extract." While the fresh inner leaf material does not cause strong gelation of alginate solutions without further concentration, the commercial dry concentrate form can be dissolved in water to form solutions that readily induce gelation.

Another common succulent species found useful in the invention, *Carpobrotus edulis*, has a similar tougher, chlorophyllic skin tissue surrounding a gel-like core. The liquid produced by pressing this plant will strongly gel alginate.

As used herein, the term "succulent" refers to any plant of the order Asparagales, family Asparagaceae, sub-family Agave; the order Caryophyllales, family Aizoaceae; and the order Saxifragales, family Crassulaceae. Specific non-limiting examples include *Agave americana, Agave angustifolia, Aave tequilana, Agave attenuata, Agave parviflora, Agave murpheyi, Agave vilmoriniana, Agave palmeri, Agave parryi, Agave victoriae-reginae, Acrosanthes, Aizoanthemum, Aizoon, Galenia, Gunniopsis, Plinthus, Tetragonia, Aptenia, Aridaria, Aspazoma, Brownanthus, Calamophyllum, Caulipsilon, Conophytum, Dactylopsis, Erepsia, Hameria, Hartmanthus, Hymenogyne, Marlothistela, Mesembryanthemum, Phiambolia, Phyllobolus, Prenia, Psilocaulon, Ruschiella, Sarozona, Sceletium, Synaptophyllum, Apatesia, Carpanthea, Caryotophora, Conicosia, Hymenogyne, Saphesia, Skiatophytum, Aethephyllum Cleretum Dorotheanthus, Acrodon, Aloinopsis, Amphibolia, Antegibbaeum, Antimima, Arenifera, Argyroderma, Astridia, Bergeranthus, Bijlia, Braunsia, Brianhuntleya, Carpobrotus, Carruanthus, Cephalophyllum, Cerochlamys, Chasmatophyllum, Cheiridopsis, Circandra, Conophytum, Corpuscularia, Cylindrophyllum, Delosperma, Dicrocaulon, Didymaotus, Dinteranthus, Diplosoma, Disphyma, Dracophilus, Drosanthemum, Eberlanzia, Ebracteola, Enarganthe, Erepsia, Esterhuysenia, Faucaria, Fenestraria, Frithia, Gibbaeum, Glottiphyllum, Hallianthus, Hereroa, Ihlenfeldtia, Imitaria, Jacobsenia, Jensenobotrya, Jordaaniella, Juttadinteria, Khadia, Lampranthus, Lapidaria* (plant), *Leipoldtia, Lithops, Machairophyllum, Malephora, Mestoklema, Meyerophytum, Mitrophyllum, Monilaria, Mossia, Muiria, Namaquanthus, Namibia, Nananthus, Nelia, Neohenricia, Octopoma, Odontophorus, Oophytum, Ophthalmophyllum, Orthopterum, Oscularia, Ottosonderia, Pleiospilos, Polymita, Psammophora, Rabiea, Rhinephyllum, Rhombophyllum, Ruschia, Ruschianthemum, Ruschianthus, Schlechteranthus, Schwantesia, Scopelogena, Smicrostigma, Stayneria, Stoeberia, Stomatium Tanquana Titanopsis, Trichodiadema, Vanheerdea, Vanzijlia, Vlokia, Wooleya, Zeuktophyllum, Cypselea, Sesuvium, Trianthema, Tribulocarpus, Zaleya, Adromischus, Aeonium, Afrovivella, Aichryson, Bryophyllum, Cotyledon, Crassula, Cremnophila, × Cremnosedum, Dudleya, Echeveria, Graptopetalum, Greenovia, Hylotelephium, Hypagophytum, Jovibarba, Kalanchoe, Lenophyllum, Meterostachys, Monanthes, Orostachys, Pachyphytum, Perrierosedum, Phedimus, Pistorinia, Prometheum, Pseudosedum, Rhodiola, Rosularia, Sedella, Sedum, Sempervivum, Sinocrassula, Thompsonella, Tylecodon, Umbilicus, Villadia*, and sub-species thereof.

Alginate

As used herein, unless otherwise or more precisely specified, "alginate" refers to alginic acid, its ionized water-solvated form, salts thereof, or any of these chemical species that have been chemically modified by processes including partial hydrolysis, esterification, derivatization, and other methods, but retain the backbone structure of repeating glucuronic and mannuronic acid units that are defining of the alginic acid molecule.

In some embodiments, the mannuronic content of the alginate on a weight basis is at least 5%, or at least 25%, or at least 50%, or at least 75%, or at least 95%.

In some embodiments, the viscosity of an 1.0% aqueous solution of the alginate as the sodium salt is at least 5 centipoise, or at least 50 centipoise, or at least 500 centipoise.

In some embodiments, the viscosity is at most 10 centipoise, or at most 100 centipoise, or at most 1000 centipoise.

The alginate may be unmodified or derivatized. If it is derivatized, in some embodiments the derivatization level is at most 90 wt %, or at most 75 wt %, or at most 60 wt %, based on the total weight of the derivatized polymer. Non-limiting examples of derivatization include esterification of acid groups, for example with propylene glycol, butylene glycol, ethylene glycol or other glycol ethers.

In some embodiments, useful concentrations of alginate for the purposes of the invention may be at least 0.01%, 0.1%, 0.2%, 0.4% or 0.5%. In some embodiments, useful concentrations of alginate for the purposes of the invention may be at most 5%, 3%, 2%, 1% or 0.75%.

Preparing Compositions of the Invention

Methods of forming aqueous synergistic rheological systems and gelled aqueous materials according to the invention will now be described in detail, followed by a description of suitable materials for use in making the solutions and materials, and then a description of methods for isolation and/or use of these materials.

Formation of Synergistic Rheological Systems

The essential elements required to form a synergistic polymer solution are as follows:

1) An aqueous solution A of alginic acid or its water-soluble salts is prepared.
2) An aqueous solution B of a succulent extract, for instance, *Aloe vera* extract is prepared.
3) The solutions are combined with agitation to mix. The synergistic rheology develops upon mixing, over the course of several seconds for small volumes. Larger volumes may take longer due to the time needed to obtain uniform mixing. At low concentrations (for fluid gels) the order of addition is less important, but generally *Aloe* is added to alginate so as to preclude formation of dense gels as alginate contacts an excess of *Aloe*.

A range of solution concentrations may be used according to the invention, and the particular range is specific to the material being used. Alginates for instance may be produced in a wide range of viscosities, this quality being dependent upon structure and molecular weight. Commercial alginates are also graded as to the ratio of glucuronic to mannuronic acid units, also related to viscosity. Without wishing to be bound to any particular conceptual framework, generally, solutions of higher glucuronic acid content alginates exhibit stronger synergistic rheology effects in the invention. Thus correspondingly lower concentrations are required to achieve similar rheological properties, for example for producing gelled materials of higher yield value, or resistance to deformation, and hence suspending capacity, (i.e., the capacity to support larger particles or bubbles, or particles of density that is more widely variant from the density of the system itself). For example an aqueous composition comprising 1% wt sodium alginate (Manucol DH, FMC Health & Nutrition, Philadelphia, Pa.) and 0.4% wt. *Aloe vera* extract (100% Organic *Aloe Vera* Whole Leaf Powder 200X, Earth Supplied Products, Naples, Fla.) at pH 5, will suspend wood shavings and common steel office staples in the bulk phase, but co-dispersed #1 size steel paperclips will slowly sink, at a rate of about 0.5 inches per minute. Dilution to 0.75% alginate and 0.3% *Aloe vera* produces a very similar product that will suspend wood shavings effectively, but staples sink rapidly. A 1.5% alginate/0.6% *Aloe vera* product will suspend the paperclips as well. Without wishing to be bound to any particular conceptual framework, use of an alginate with a higher glucuronic to mannuronic acid content ratio (such as Manugel GHB, FMC Health & Nutrition, Philadelphia, Pa.) would produce similar rheological systems at a relatively lower concentration.

Aqueous solutions of *Aloe* or other described succulent extracts alone typically exhibit water-like rheology, even at concentrations 20-fold higher than freshly extracted plant juice. When introduced to alginate, higher concentrations of succulent extract induce more dramatic rheology changes, and can aid in rapid gelation of droplets to produce beads.

The synergistic polymer solutions of the invention are typically stable to freeze/thaw cycling, and may be brought nearly to a full boil without apparent substantial alteration of their rheological characteristics. The synergistic viscosity increase appears to be maximal at between pH 6 and pH 4 for dilute solutions, e.g., 0.5% to 2% solids content. Typically, the pH of compositions according to the invention will be at least 2.5, 3.0, 3.5, or 4.0. The pH will typically be at most 9.0, 9.5, 8.0, 7.5, or 7.0. Viscosity data (mPa-s) for a total dissolved solids range from 0.25% through 1.5% and a 5 point range of alginate/*Aloe* ratios, presented in Table 3, show peak synergistic effect at a 1:1 ratio in all cases. It is of interest that 25% alginate fraction is not symmetric with 75% alginate fraction data above 1% total dissolved solids. Without being bound to any particular interpretation, it appears that until there is enough *Aloe* to affect some critical fraction of the alginate, the viscosity of the system is not strongly influenced.

In some aspects, the rheological liquid systems of the invention may produce a solution viscosity of at least 1 mPa-s, 10 mPa-s, 50 mPa-s, 100 mPa-s, or 500 mPa-s. In some aspects, the rheological liquid systems of the invention may produce a solution viscosity of at most 10000 mPa-s, 5000 mPa-s, 2500 mPa-s, 1000 mPa-s, or 750 mPa-s.

Table 3 shows solution viscosity (mPa-s) results for a range of *Aloe*-alginate solution concentrations. Columns group solutions by total solids (*Aloe*+alginate) content, while rows group solutions by alginate fraction, i.e., 0% alginate corresponds to 100% of the dissolved solids being *Aloe*. The maximal viscosity is seen at a total dissolved solids level of 1.5% wt, in which the alginate fraction is 50%, i.e., the solution comprises 0.75% *Aloe* solids and 0.75% alginate solids.

TABLE 3

| | Total dissolved solids (percent of formulation) | | | | | |
|---|---|---|---|---|---|---|
| | Alginate fraction of solids | | | | | |
| | 1.50% | 1.25% | 1% | 0.75% | 0.50% | 0.25% |
| 0% | 2 | 2.5 | 2 | 2 | 4.5 | 4 |
| 25.00% | 562.5 | 135 | 65 | 12 | 12 | 6 |
| 50.00% | 7500 | 4900 | 3700 | 950 | 86 | 6.5 |
| 75.00% | 85 | 42 | 30 | 10 | 10 | 5.5 |
| 100.00% | 106 | 58 | 43 | 12 | 12.5 | 7.5 |

The compositions may further comprise a dispersed material suspended therein, for example a liquid, gaseous, or solid particulate material. In some embodiments the dispersed material may be partially or fully insoluble in the continuous phase, or may be complex materials such as microcapsules or a cells or living tissues. In some embodiments, for example, 1% wt aqueous sodium alginate and 1% wt. aqueous *Aloe* vera extract at pH 5, the dispersed material does not visibly rise or sink in the composition when left undisturbed for more than one month at 50° C. Such compositions may be of particular advantage in avoiding contact between pockets of the suspended dispersed material, as for preventing aggregation of particles or interaction between cells.

Without being bound to a particular interpretation, if the quantity of dispersed material exceeds, for example, to greater than about 70%, the continuous phase comprising the rheologically synergistic system of the invention may become constrained to the interstitial regions between pockets of the dispersed phase, as is commonly understood in the study of foams, pastes, slurries and loaded emulsions, and generally, deformable solids such as those classified rheologically as Bingham plastics. The extreme shear-thinning behavior of the present rheological systems may therefore confer particular advantage in formation and stabilization of such systems.

The compositions may further comprise a material dissolved in some or all of the components. For example, in some embodiments, addition of humectants, such as glycerin or water-soluble antioxidants, may provide additional benefits when applied to skin.

In some compositions according to the invention, the amount of succulent extract relative to alginate is at least 0.1%, 0.5%, 1%, 2%, 4%, 8%, 10%, 20%, 40%, 60%, 80% or 100%. In some compositions, the amount is at most 1000%, 500%, 200% or 100%, in all cases on a dry basis.

In some compositions, the combined solids content of succulent extract plus alginate is at least 0.01%, 0.05%, 0.1%, 0.25%, or 0.5% wt. In some embodiments, the content is at most 10%, 5%, 2%, 1%, or 0.75% wt.

In some embodiments of the invention, it is desirable to limit the amount of multivalent metal cations present in the composition or its constituent solutions, relative to alginate. For example, it may be desirable that the amount(s) of such metals be low enough as to be less than an amount effective for gelling the alginate in the absence of the succulent extract. Examples of cations that may be limited include calcium, magnesium, barium, zinc, copper, and aluminum. Any one of these individually, or any combination of two or more of them, or all of them in total, may be limited. In some embodiments, the upper limit relative to alginate is 0.2%, 0.1%, 0.05%, 0.025% or 0.01%.

In some embodiments, anionic surfactants are excluded from the composition. In other embodiments, anionic surfactants may be tolerated as long as the amount, relative to alginate, is no more than 5%, 1%, 0.5%, 0.1%, or 0.05%. In some embodiments, calcium chelators, for example ethylene diamine tetraacetic acid (EDTA) or soluble salts thereof, are excluded from the compositions.

In some embodiments, components that contribute additional calcium ions are included in the composition, and these may include materials that liberate calcium ions under selected conditions, for instance at a selected solution pH or temperature, while not contributing free calcium ions to the solution at other conditions, such as at a different solution pH or temperature. For example, some salts or complexes containing calcium, such as calcium chloride, calcium citrate, calcium acetate, calcium sulfate, or the complex formed by EDTA and calcium, may be included in quantities relative to alginate of no more than 0.1%, 1%, 2%, 5%, or 10%.

In some embodiments, antiperspirants, including aluminum chlorohydrate and other aluminum compounds with similar activity are excluded from the composition. In other embodiments, these materials may be tolerated as long as the amount, relative to alginate, is no more than 5%, 1%, 0.5%, 0.1%, or 0.05%.

In some embodiments, antifungal or antidandruff agents, including zinc pyrithione and other zinc compounds with similar activity are excluded from the composition. In other embodiments, these materials may be tolerated as long as the amount, relative to alginate, is no more than 5%, 1%, 0.5%, 0.1%, or 0.05%.

In some embodiments, quaternary amines are excluded from the composition. In other embodiments, these materials may be tolerated as long as the amount, relative to alginate, is no more than 5%, 1%, 0.5%, 0.1%, or 0.05%.

Formation of Gelled Materials

Gelled materials may be formed or cast by combining an aqueous precursor liquid, for example 1% aqueous sodium alginate solution, with a curing liquid comprising a succulent extract. The interaction between the precursor and curing liquids causes the precursor liquid to set into a gel. Without wishing to be bound by any particular model, the strength and rigidity of the gel is understood to increase with increasing concentration of each of the solutions. However, the ratio of total succulent content to alginate content plays an important role at lower concentrations. For example a 0.2 mL droplet of 1% aqueous alginate introduced to a 5 mL bath of 1% aqueous *Aloe vera* solution will eventually form a bead very similar to that resulting from introduction of an identical droplet to a 1 mL bath of 5% *Aloe* solution, but the process takes substantially longer, for instance tens of minutes as compared to seconds.

A composition comprising a 1:1 ratio of *Aloe vera* to alginate at a total solids content of about 1% or less shows strong synergistic rheological thickening, but is readily dilutable with water. In contrast, firm, solid, non-fluid gels tend to form when *Aloe vera* content is present at greater than about a 2:1 ratio to the alginate content and the alginate concentration is greater than 1.0% wt. These firm gels will not dilute or resolubilize by exposure to water, even at elevated temperature, for example 50° C. for 2 months or more. Although droplets of a 1% alginate solution can slowly form gel particles when introduced to a bath of 1% *Aloe* solution wherein excess *Aloe* is available, simply combining equivalent volumes of the two solutions results in a suspending rheological system, not a gel, apparently due to insufficient *Aloe vera* content for formation of a firm gel. Without being bound to a particular explanation, The inventors note that formation of a non-dilutable gel versus a dilutable fluid appears to be a function of both the concentrations and the relative ratio of the alginate and succulent components. For example, a non-dilutable gel may be formed by a sufficiently high concentration of the components even when the ratio of the components is such that at lower concentrations the same ratio forms a dilutable rheologically synergistic fluid. Thus concentrating the dilutable fluid systems described herein, for example by evaporation, can produce a solidified, non-dilutable gel product. That is, the gel product will not dissolve in water over a period of at least 60 days, even if the water is heated.

Without being bound to any particular interpretation, the transition to thickening and then to gelation of the alginate component of the invention appears to be accomplished incrementally by addition of sufficient succulent extract, meaning that any rheologically synergistic fluid systems of the invention should be gelled by the introduction of sufficient additional succulent extract component. Thus any of the methods and products involving gelation of alginate described herein may be similarly accomplished when a combined succulent-alginate rheologically synergistic fluid is substituted for the alginate precursor liquids described herein.

As described below, a system of similar composition possessing comparable rheological properties may also be formed by direct dissolution of a single dry composition into water.

Precursor Liquid

The precursor liquid of the invention comprises aqueous alginic acid and/or ions and salts thereof. The terms "alginic acid" and "alginate" are used interchangeably herein, unless the context clearly indicates that one of these is specifically meant.

In another aspect of the invention, alginate, understood to be the gelling component, may be combined with other materials. Without being bound to an interpretation, the additional materials now described are not understood to participate in the gelation process, but may modify, for example, the rheological properties of the precursor liquid. Such materials may also dissolve out of the gel particles after formation, thereby modifying the physical properties of the particles. Examples of additional materials useful for inclusion in the precursor liquid include but are not limited to: acacia gums, agar, polyacrylic acid, albumins, carbomers, casein, cassia gum, cellulose gums, chitosan, chondroitin, curdlan, gelatin, dextran, fibrin, fulcelleran, gellan gum, ghatti gum, guar gum, gum tragacanth, heparin, hyaluronic acid, karaya gum, locust bean gum, pea protein, pectin, polyoxyethylene-polyoxypropylene and other synthetic block copolymers, pullulan, starch, soy protein, tara gum, whey protein, xanthan gum, and zein, and ions and salts of these materials. In some embodiments these exemplary additional materials may constitute at least 0.01%, 0.1%, 1.0%, 5%, or 10% relative to the alginate component by weight. In some embodiments these exemplary additional materials may constitute at most 90%, 50%, 25%, 15%, or 10% relative to the alginate component by weight.

Formation of Gel Beads or Particles

In one aspect of the invention, droplets of a precursor liquid (A), comprising for example 1% sodium alginate, are introduced into a bath of a second aqueous solution (B) comprising an aqueous solution of a succulent extract, for example 5% *Aloe* extract, which induces the droplets' in-situ gelation. In another aspect of the invention, solutions A and B may be exchanged such that droplets of the succulent extract fall into a bath of alginate. In either case, the interaction of the solutions causes gelation localized to the introduced droplets. Without being bound to a particular interpretation, it appears that local gelation occurs and particles are formed where the alginate component interacts with an excess of the succulent component, i.e., more than about 2:1 proportional to alginate.

As a model system, a 1% sodium alginate (Manucol® DH, FMC Health & Nutrition, Philadelphia, Pa.) solution is introduced through a hypodermic needle as droplets falling into a 5% *Aloe vera* solution (100% Organic *Aloe Vera* Whole Leaf Powder 200X, Earth Supplied Products, Naples, Fla.). As the droplets enter the bath, they rapidly gel to form clear, firm beads.

A variety of factors influence the average size and size dispersion of the particles thus formed, including, but not limited to the rheological properties of the precursor liquid, dispensing pressure, and orifice size. In practice, droplets to be gelled by the present method may be formed by any method known to those skilled in the art of producing droplets, mists and sprays. Larger particles or objects may be formed by introducing larger volumes of the alginate solution to the *Aloe* solution, as by pouring, injecting, or otherwise introducing the solutions into contact by rapid or gradual means. Particles may be formed by co-spraying the components, spraying one component through an aerosol or flowing sheet of the other component, crossed-streams of the respective components, co-emulsion of the components in a liquid phase, introduction of frozen solid objects of one phase to a bath of the other phase, removal of a physical barrier between the two components, or by any other means of contacting a volume of one component with a volume of the other component.

In some aspects of the invention, the particles formed may be at least 100 nm, 1 µm, 10 µm, 100 µm, or 1 mm in maximum dimension. In some aspects of the invention, the particles or objects formed may be at most 1 m, 100 cm, 10 cm, 1 cm, or 10 mm in maximum dimension.

In some embodiments, at least 90 wt % of the particles are spherical to within 50%, 25%, 15%, 12%, 10%, 5%, 1%, 0.5% or 0.1%. By this, it is meant that the largest dimension of a given particle is greater than the smallest dimension by no more than the recited percentage.

The gelling components of the precursor liquid comprise alginic acid and/or ions or salts thereof. The properties of the resulting gel particle may be manipulated by inclusion of other non-gelling materials, for example other hydrocolloids that influence the rheology of the precursor liquid, including lower levels of *Aloe* extract itself, or other water-soluble agents that may influence the strength of the resulting gelled particle, possibly by partially inhibiting the gelation process. The properties of the resulting gel particles may also be manipulated by addition of other materials that gel or solidify due to thermal or other mechanisms. For example, inclusion of a thermally gelled carrageenan such as Gelcarin® PC-911 (FMC Health & Nutrition, Philadelphia, Pa.) or a protein subject to thermal or chemical denaturation, for example ovalbumin, in the alginate solution used to form a gel particle results in a particle that can be further modified by post-formation heating or cooling processes.

In another aspect of the invention, additional materials may be dissolved or dispersed in the precursor liquid, such that after gelation, these additional materials are entrapped in the resulting bead or particle. Such materials may additionally be selected to alter the rheology of the precursor liquid by their presence.

Suitable Payload Materials for Entrapment in Beads or Particles

In some embodiments of the invention, a wide variety of payload materials may be entrapped in the particles thus produced. The primary constraints upon what may be entrapped or encapsulated within the particles are that that entrapped material must be of smaller dimensions than the particles produced, and that the entrapped material must be miscible or dispersible within the precursor phase. Generally any material that may be dispersed in the precursor liquid without preventing formation of droplets or preventing subsequent gelation is suitable for entrapment. In some aspects of the invention, entrapped payload materials may constitute at least 0.01%, 0.1%, 1%, 10% or 25% by weight of the droplet composition. In some aspects of the invention, entrapped payload materials may constitute at most 99%, 90%, 75%, 50% or 30% by weight of the composition.

A variety of payload materials, i.e., active materials, may be entrapped in the particles of the present invention, providing benefits in use that are in addition to the benefits afforded by the *Aloe vera* and alginate components. For example, beneficial payload materials might include, but are not limited to: abrasives, antibacterial agents, deodorants, pigments and colorants, sunscreen actives, fragrance, pH indicators, living cells or organisms, seeds, spores, minerals, entrapped gases, surfactants, hair conditioning agents, bleaching agents, skin lightening agents, keratolytic agents, anti-inflammatory agents, emollients, antioxidants, vitamins, flavorants, proteins, nutritional supplements, medicaments, waxes, solvents, hormones, growth factors, immunomodulatory agents, chemotherapeutic agents, magnetic particles, semiconductors, photo-responsive materials, insect repellents, fertilizers, fracking proppants, defoliants, herbicides, and/or pesticides.

In another aspect the invention provides a highly shear-thinning aqueous fluid that may be sprayed, and when sprayed, readily adheres to surfaces in a gel-like film that resists flowing and/or dripping. The highly viscous, almost gelled rheology of the fluid prevails under conditions of low shear, e.g., tilting a container, but under high shear readily forms a fine, atomized mist, as in a trigger or pressure sprayer. Upon leaving the sprayer, however, the shear forces are largely removed and the material rapidly returns to a gel-like state, which it retains upon depositing on a surface, even when many such droplets coalesce. The droplets may momentarily liquefy upon impact, and then regel. Subsequent sprays cause more drops to impact and liquefy, some of which overlap with previously deposited (and now gelled) droplets, and they either simply wet upon those gelled droplets and/or possibly liquefy the previously deposited droplets or layer as well, but not enough to cause bulk flow in response to gravity. In some cases it is possible to deposit coatings several mm thick onto a vertical surface, depending upon the gel strength of the particular composition being sprayed.

Transition of Rheologically Useful Fluid to Insoluble Gel State

As noted above, at high concentrations of the alginate and succulent extract, a firm gel is formed that is resistant to re-dissolution by water. Nonetheless in some ratios of the components, at low concentrations the resulting composition may exist as a sprayable fluid, while at higher concentrations, the same relative combination of components may form a water-insoluble gel. A useful product may be thus formed, that may be applied in low concentrations as a convenient aqueous liquid, but after drying, concentrates to form a water-insoluble film. In particular a composition comprising 1% aqueous sodium alginate and 1% *Aloe vera* extract may be sprayable with a common cosmetic fingertip sprayer (example 24-410 Black Fine Mist Sprayer w/ 6⅞" Tube, Item ID: S005, Container & Packaging Supply, Eagle, Id.), or household trigger-spray (example 8-400 Black Sprayer w/ Spray/Stream & 9¼" Tube Item ID: S038, Container & Packaging Supply, Eagle, Id.) commercial dispenser.

Intermediate Gel State that May be Fluidized by Shear

In some embodiments of the invention, materials with properties intermediate to the extremes of water-insoluble firm gels and water-dilutable shear-thinning fluids may be formed. For example, it is possible to reduce the gel strength of the alginate through incorporation of components that do not exhibit gelling or thickening behavior with *Aloe* extract, for example sodium carboxymethylcellulose, or any other polymer that similarly does not thicken with *Aloe*. Thus, in some embodiments beads may be formed from such a diluted alginate solution, that are readily sheared to liquefaction by pumping through a spray nozzle (as described above) or a self-foaming dispensing pump (for example 30 mm Natural Foamer w/ 3¼" Tube, Item ID: DP102, Container & Packaging Supply, Eagle, Id.). Thus, products may be formed that contain visible beads loaded with pigment or dye such that the beads "disappear" upon undergoing the high shear conditions of dispensing by spraying or pumping to form a mist or foam. The beads may be prepared as described in the examples below, and then partially dehydrated or densified to form a granular product that is robust to transport, mixing, and pumping for a selectable time period after which the beads are fully rehydrated to provide the desirable liquefaction under elevated shear described above. Beads may be dehydrated by introducing them into a solvent bath, for example ethanol or isopropanol, or any other solvent that will effectively dissolve water, removing it from the gel matrix without dissolving, reacting with, or otherwise disrupting the structure of the bead. The resulting partially dried beads are thereby reduced in weight by 10-50 fold, and are more robust in this densified form, such that they may be readily handled or mixed into a viscous product without breakage or shear sensitivity. Immediately on introduction to an aqueous system, they begin to hydrate but are tough enough to be mixed or dispensed through a nozzle, as for filling a container with a product, for at least 30 minutes in plain water or many hours in, for example, the gel suspending compositions described herein. The beads may also be fully dried by evaporation, producing a yet further dried product form, that nonetheless rehydrates to a shearable gel. A person of ordinary skill in particle drying processes will be able to dry the beads described herein by a wide variety of methods, including but not limited to suspending in a fluid bed, spray drying of partially densified beads, spreading onto a surface, vacuum drying, and so forth.

As used herein, a "rehydratable gel" is one that, upon exposure to water at room temperature (23° C.), swells to a maximum size but will not swell further upon longer exposure, nor will it self-disperse in water or dissolve such that no gel particles remain.

Rheological Systems of the Invention as Dispersed Phases

The rheological properties of the compositions of the invention may also be exploited in formation of rheologically stabilized dispersions wherein the succulent-alginate systems form the dispersed phase in a composition rather than the continuous phase. The continuous phase of such compositions must be immiscible with the dispersed aqueous succulent-alginate phase.

The shear-thinning rheology of the succulent-alginate system provides advantages in forming and stabilizing water-in-oil type emulsions. For example a product comprising equal volumes of 1% alginate combined with 1% *Aloe* solutions may be dispersed in an oil phase, for instance icosane, and this process may be facilitated by use of a low hydrophobic-lipid-balance (HLB) surfactant, for example sorbitan monooleate (Jeechem SMO, Jeen International Corp., Fairfield, N.J.). As shear is applied to such a dispersion, the viscosity of the synergistically thickened aqueous phase drops, facilitating formation of smaller droplets. However, when shear forces are removed from the system, the aqueous droplets rapidly recover their high viscosity, stabilizing the system against coalescence and ripening phenomena, as compared with similar emulsions formed without the shear-thinning polymer system.

In some embodiments the aqueous succulent-alginate phase may constitute at least 0.1%, 1%, 5%, 10%, or 20% wt of the water-in-oil dispersions of the invention. In some embodiments the aqueous succulent-alginate phase may constitute at most 95%, 90%, 80%, 50%, or 30% wt of water-in-oil dispersions of the invention.

Controlling the Gelation Activity of Calcium Ions

Without being bound to any particular interpretation, the inventors believe that calcium present in the succulent components of the present invention contributes to gelation, but is not the only source of the rheological changes induced in alginate solutions when the two materials are combined, as demonstrated by the different viscosities of systems with equivalent calcium levels in the presence or absence of the other succulent components. *Aloe vera* and other succulent extracts are complex systems containing a rich variety of materials, including amino acids, anthraquinones, enzymes, minerals, vitamins, lignins, monosaccharides, polysaccharides, saponins, and sterols, any one or more of which may influence the rheological properties of the composition.

Nonetheless, calcium ions can still affect the rheological properties of the overall system, even though this effect may be modulated by the *Aloe* components. Thus, rheological properties can be modified by controlling the levels of calcium ions available to the systems. For example, a material capable of sequestering calcium ions may be included. Sequestration of calcium ions in an *Aloe* solution by, for example, EDTA, can substantially reduce the viscosity of the resulting system when it is combined with alginate solutions. Addition of calcium ions to *Aloe* solutions can conversely increase the viscosity of the resulting aloe/alginate system. Such manipulation is further described below.

Partially Dehydrated Precipitated Bulk Gel Compositions

While complete drying of the gel composition produces a rehydratable but non-dilutable, non-water-soluble gel, a partially dehydrated product may be formed in a manner similar to the partial drying of the beads described above by introduction of a solvent that dissolves water but does not dissolve the alginate/*Aloe* gel components. The gelled complex is thus precipitated in the resulting liquor. For example, a shear thinning suspension may be formed as in Example 1, and to this material a volume of 95% ethanol (ESP SDA-40B, Earth Supplied Products, Naples, Fla.) is added so as to increase the total volume by 50%. If this mixture is stirred, the *Aloe*/alginate gel system will form a hazy, lumpy mass with a gelatinous texture. This mass may be readily strained and pressed to produce a fibrous mat of the precipitate, roughly 10% of the weight of the original material. This mat may be further crumbled into smaller granules and air dried to 5% of the original solution weight, thereby producing a 20× concentrate. This concentrate may be added to water and with stirring will rapidly rehydrate to produce the original water-dilutable fluid gel of the original system. Such a system confers great advantage as it provides a single material that may be added to water, quickly rehydrating to form a gel, as compared to the alternative of dissolving alginate and *Aloe* solutions separately and then combining them to form the material of Example 1.

Challenges to Forming Dry *Aloe*/Alginate Composite Powders for Direct Use

As described herein, when the synergistic *Aloe*/alginate system of Example 1 is dried to, for example, 20% of its original weight, the concentrated polymers form a gel that is no longer water-soluble, but only rehydratable as a swelled gel of a fixed shape. That is, the dried product cannot be simply rehydrated to reproduce the material of Example 1. But a fully desiccated, dry powder product that could be combined with water to produce a system similar to Example 1 would be useful and valuable as it could be transported dry at low weight and readily constituted at the point of use in a single container by simply adding water and mixing. But the inventors have found that a simple direct mixture of dry alginate powder with dry *Aloe* powder to form this desired composition does not in fact reproduce the material of Example 1. Rather, that system produces a somewhat thickened material of granular appearance, with many discrete particles of alginate surrounded by a layer of a gel phase. Apparently the *Aloe* powder dissolves rapidly relative to the alginate material, even when the alginate is very finely ground as by a mortar and pestle and well wetted with ethanol or glycerin to promote easy dispersion. As described above, alginate solutions are thickened by *Aloe* solutions, and without being bound to a particular interpretation, it appears that alginate particles upon beginning to dissolve are entrapped in the nascent solution, which is gelled upon contact with the *Aloe* solution. Indeed, the inventors were unable to effectively dissolve alginate particles in pre-formed *Aloe* solutions above about 0.10%/0-0.25%, depending upon the *Aloe* source.

Manipulation of Calcium Levels

Without being bound to a particular interpretation, the inventors believe that calcium plays a role as one of the constitutive components of the *Aloe* solution that is involved in forming the synergistic rheological systems of the present invention. Therefore, while other components of *Aloe* (and other succulents) solutions are also observed to participate in the rheological synergy, the calcium level may be manipulated so as to push the system toward promotion or inhibition of selected rheological properties, in particular viscosity and shear-thinning behavior.

Similar to the inhibition of dissolution of alginate in *Aloe* solutions, alginate will not effectively dissolve in a calcium solution containing more than about 0.01%, instead forming similar gel-coated particles that are ineffective in producing an extended, continuous gel structure characteristic of a useful suspending agent.

Solutions of *Aloe* (and generally succulents described herein) solutions below about 0.25% concentration, as shown in Table 3 above, do not substantially thicken alginate solutions, and consistent with the interpretation presented above, at such low *Aloe* concentrations alginate will in fact dissolve readily in these solutions. If an additional source of calcium is introduced to such an *Aloe*/alginate solution, viscosity may be readily induced due in part to calcium and in part to *Aloe*. Indeed a composition may be formed by supplementing a 0.25% *Aloe* solution with an additional 0.01% dissolved calcium (for instance from calcium chloride) content. If either of these components alone is present, mixing the solution with an equal volume of 1% alginate solution drops the viscosity of the alginate solution due to dilution. However, although neither component is individually present in sufficient quantity to thicken the alginate solution, in combination they will produce dramatic thickening when combined with the 1% alginate. Without being bound to a particular interpretation, while the *Aloe*/alginate synergistic systems taught herein demonstrate different behavior than calcium alginate gels, *Aloe*/alginate systems may be modified by manipulating calcium levels to produce new systems with their own specific rheological properties.

The ability to increase the calcium level so as to trigger thickening of an *Aloe*/alginate system that is itself below the concentration threshold required for thickening makes new combined products possible. Similarly, calcium may be removed by, for example, sequestration using EDTA, such that a level of *Aloe* that would ordinarily induce overt thickening of an alginate solution may be reduced below that activity threshold. As EDTA sequestration of calcium is pH-dependent, the resulting system exhibits pH-dependent thickening. As pH drops below about 4.5, calcium previously bound by EDTA is liberated and then able to participate in the rheological system, raising the synergistic effect to the full strength for that quantity of *Aloe*. Sequestrants that may be appropriately used to control calcium levels in exemplary systems include not only EDTA, but also iminodisuccinic acid, polyaspartic acid, ethylenediamine-N,N'-disuccinic acid, methylglycinediacetic acid, L-glutamic acid N,N-diacetic acid, tetra sodium salt, or combinations thereof.

Dry Powders for Direct Use

By manipulating the availability of calcium to participate as one of the components of the *Aloe*/alginate synergistic system described herein, it is possible to produce dry powder forms of the system suitable for direct dispersion into water to form systems with rheological behavior similar to those of Example 1. For example, a dry composition may be formed comprising 30% *Aloe vera* solids, 30% disodium EDTA, and 35% alginate (Manucol DH, FMC Biopolymers, Philadelphia, Pa.). A 1.0 g aliquot may be added directly to 100 mL water by any customary method (e.g. direct dispersion, or pre-wetted with an alcohol or glycerin) and dissolves to form a clear solution of about 30-40 cps viscosity, in which bubbles rise rapidly and any particles introduced sink rapidly. If this solution is acidified by addition of approximately 3 mL of a 10% citric acid solution, as the pH drops below about 4.5, the viscosity abruptly increases to the 3000-4000 range, presumably as the sequestered calcium is liberated by the EDTA and thus enabled to participate in the synergistic rheological system.

Another dry composition may be formed comprising 85% alginate, 5% *Aloe*, and 5% calcium citrate, a calcium salt with poor water solubility at neutral pH, but enhanced solubility at low pH. If 1 g of this dry composition is hydrated in 100 g of stirring water, a clear solution is formed at about 30 cps viscosity over the course of several minutes. The *Aloe* content of this solution is well below the range at which substantial synergistic thickening would be observed with the alginate, and the components smoothly go into solution. It is understood that the calcium citrate equilibrium at near neutral pH is such that very little calcium is liberated from that component, and is further inhibited by calcium contributed from the *Aloe* component. However, as the alginate component dissolves, this mildly acidic material induces a drop in pH, that is understood to promote dissolution of the calcium citrate. If the initial low viscosity solution is left to hydrate for an extended period of hours, the viscosity is observed to climb substantially and after about 10-12 hours is found to be in the vicinity of 4000 cps. Alternatively, if the system is dissolved and then rapidly acidified by the addition of about 1.5 mL of 10% citric acid, it very rapidly thickens to a similar high viscosity product. Whether left to slowly self-acidify or rapidly pushed to this state, the properties of the resulting product are similar to the composition of Example 1.

Triggered Viscosity Change

The ability to induce a rapid, triggered shift from a low viscosity system to a higher viscosity system is of particular utility in the manufacture of bulk consumer products with suspended particles or droplets, in which the shear-thinning properties of the suspending agent are desired in the finished product but may pose difficulty during manufacture. For example, if droplets of oil are desired to be suspended uniformly in a product, but must be initially dispersed, as in an emulsion, it is useful to have an easily mixed solution that can be readily stirred en-masse, so that a single mixing head can process a large container. The product of Example 1 is so viscous when not under shear that in a large container, mixing might be strong in one area but other areas would remain essentially gelled and these "dead spots" would not be uniformly mixed. In the present example, the low viscosity system could be readily mixed to uniformity and then acidified to rapidly thicken, preventing separation due to density differences between the dispersed oil phase and the continuous aqueous phase. The system might also be triggered by addition of an appropriate quantity of a source of calcium ions.

Surfactant Products

In some instances it is useful to provide the rheological properties of the present inventive system in the context of a surfactant product, and examples are provided of systems that support foam production, sprayability, adherence to surfaces, and other benefits. It is well known to formulators of ordinary skill working with surfactants, and particularly the class of surfactants described as anionic surfactants, that water hardness sensitivity, and specifically calcium sensitivity, can play an important role in surfactant performance as well as the performance of other components in a particular detergent system. As the present system does contain calcium, as described, it might be expected that some aspects of surfactant performance could be affected. However, as used for common hand washing and surface cleaning, surfactant systems can be developed that retain most if not all of the apparent benefits of the surfactants and further possess the desirable qualities of the presented rheological systems. Nonetheless, some evidence of calcium interaction with the surfactants is evident. Specifically, simple addition of useful levels of some surfactants can cause rapid thinning of an initially viscous system. Not wishing to be bound by a particular interpretation, many effects may be responsible for this thinning, but calcium-surfactant interaction is one such effect and therefore experiments were performed in which additional calcium was introduced to such a surfactant-thinned rheological system. Substantial recovery of the rheological characteristic was achieved, while retaining the apparent benefits of the surfactant system in terms of foam production, foam stability, optical clarity, and cleaning capability.

Solutions of anionic surfactants were found to attack gel beads such as those described in Example 9, leading to breakage of the gel structure and softening or failure of the beads. Use of a calcium-supplemented gel such as that described in Example 58 precluded such attack. Without being bound to a particular interpretation, the anionic surfactant may destabilize the beads by acting as a calcium sequestrant, reducing the firmness of the beads' gel structure, and generally it may be presumed that bead instability caused by calcium sequestration associated with any other material may be ameliorated by using a calcium-enriched formulation as in Example 58.

Cationic surfactants are well known to form ionic associations with negatively charged materials, and this can sometimes be exploited, but can also cause problems, especially when these are added to formulations containing additional anionic solvated materials. The materials of the present invention are moderately tolerant of cationic surfactants and useful quantities of these materials may be added to surfactant systems described herein providing benefits commonly ascribed to these materials. High use levels (for example above 0.1%) of monoalkylammonium quaternary amines, for instance benzalkonium chloride, can cause apparent partial or complete complexation and precipitation of the alginate fraction of the systems described herein, inducing visible haziness and turbidity and resulting in loss of viscosity.

Supplementation of the alginate component of the composition can prevent viscosity loss. For example gradual addition of 20 mL of a solution comprising 0.625% *Aloe* (Earth Supplied Products, Naples, Fla.) solids and 0.250% benzalkonium chloride (Spectrum Chemicals, New Brunswick, N.J.) in water to 30 mL of a stirring solution of 1% sodium alginate, and then adjusting to approximately pH 6 by addition of about 0.5 mL 10% citric acid solution (Earth Supplied Products, Naples, Fla.), produces a viscous shear-thinning solution with properties comparable to those of the product of Example 1, except that the product formed with inclusion of benzalkonium chloride is substantially hazy, and visually nearly opaque.

Surfactants are used in a wide variety of applications and fields including but not limited to biology, chemistry, fuels, consumer products, mining, construction, paints and coatings, and many others. Surfactants can further act as solubilizers, increasing the water solubility of water-immiscible materials to create clear solutions. Some materials may not be classified as surfactants but yet may possess surfactant activities, for example many proteins and polymers can support the formation and stabilization of droplets of a hydrophobic phase within a continuous aqueous phase or vice-versa. Other materials are more formally classified as surfactants and are conveniently classified by their relative tendency to dissolve as ions in aqueous material, as anionic, cationic, non-ionic, or amphoteric or zwitterionic. Examples of such materials include but are not limited to the following. Anionic surfactants include alkyl-, aryl-, alkyl aryl-, and alkyl ether-modified sulfonates, sulfates, phosphates, carboxylates, iesethionates, glutamates, lactylates, sarcosinates, taurates, and sulfosuccinates, as well as lignin sulfonates, and fatty acid soaps. Cationic surfactants include quaternary monoalkylammonium salts, amido-amine salts, and polyquaternary amines. Nonionic surfactants include fatty alcohols, fatty alcohol alkoxylates, alkyl-, aryl-, alkyl aryl-, and alkyl ether-modified ethoxylates, glucosides, polyglucosides, glyceryl esters, sorbitan esters, polyoxyethylene ethers, ethanolamines, amines, amine oxides, imidazolines, glucosamides, and block copolymer ethers. Amphoteric or zwitterionic surfactants include amidoalkyl betaines and sultaines, alkyl sulfosuccinamides. Other specialized classes of surfactants are continually developed, for example Gemini bifunctional surfactants. Any and all of these surfactants and combinations thereof are expected to be useful in combination with or as components of the compositions described herein.

Addition of Organic Solvents

Many useful products contain solvents besides water, for any of a variety of reasons. Non-limiting examples of reasons to include an organic solvent may be to help dissolve additional materials for inclusion in a product, to dissolve materials to which a product may be applied, to apply coatings, to provide cleaning effects or emolliency effects, or to impart specific optical, mechanical and/or physical properties to a system.

Very frequently polymeric thickening systems used as suspending agents, for instance, are strongly affected by the addition of organic solvents. Addition of organic solvents may change a variety of the properties supporting a polymer's solubility in the overall product, for example the polarity of the continuous phase, which in turn may influence polymer-polymer interactions responsible for the rheological properties of the system. This may lead to precipitation, altered viscosity or response to shear among other properties. Very surprisingly, the rheological properties of the shear-thinning aqueous systems of the present invention appear to be only very slightly affected by the addition of a wide range of commonly used organic solvents. While particular components of certain systems may have higher or lower solubility in the presence of dispersed or completely dissolved organic solvent, frequently the organic solvent has little or no apparent impact upon the system's suspending capabilities and shear-thinning behavior.

Fully immiscible organic solvents may readily be suspended as emulsified droplets in a separate phase. The present invention may provide compositions having a safe, water-based continuous phase that can be used to dispense such organic solvents, for instance hydrocarbons, potentially reducing concerns of flammability or volatile hydrocarbon content while nonetheless being shelf stable and capable of being sprayed onto a vertical surface. The non-drip aspect of such a spray may be of particular utility for cleaning or other surface treatments.

However, some organic solvents in high concentration can induce precipitation of a concentrated gel fraction of the system. For instance, as described above, addition of 95% ethanol or similar short chain alcohol at a 1:2 ratio with the aqueous gel system of Example 1 causes rapid separation of a concentrated polymer suspension that can be mechanically pressed to eject additional solvent, producing a fibrous solid accounting for about 10% by weight of the original solution. This solid will rapidly redissolve if dispersed in water and stirred, reforming a system with very similar rheological properties to the system of Example 1. The precipitation and re-suspension just described effectively rids the system of additional visibly colored components, producing a very clear and comparatively colorless final solution.

While some organic solvents can induce precipitation, others, for instance glycerin, can be added to extensively dilute the system without inducing any abrupt change in the system rheology. Adding glycerin to the gel system of Example 1 to for instance a 20% glycerin content does not result in dramatic changes to the suspending capacity of the system. Continued addition of glycerin sufficient to reach a 50% glycerin content produces some thinning, apparently by simple dilution, but the composition is still strongly suspending. A wide variety of dispersed or dissolved organic solvents are similarly compatible with the systems herein described, including but not limited to: alcohols, acetates, acetone, amides, carbonates, ethers, esters, aliphatic and aromatic hydrocarbons, and glycols, glycol ethers, and ketals. In particular the systems described herein show good compatibility with so-called "green" or "alternative" organic solvents, i.e., those made from renewable resources and made using processes that attempt to minimize environmental impact. Many of these alternative organic solvents are made from plant-based feedstocks. Without being bound to a particular understanding, many such materials are higher in solvent polarity due in part to oxygen content, and this may impart particular compatibility with the aqueous systems described herein.

In particular methyl esters of fatty acids, lactate esters such as ethyl lactate, and plant-extracted terpenes such as limonene, are found to be readily compatible at useful levels (i.e. up to at least 20%). Not all organic solvents are highly compatible. For example, addition of 10% N, N-dimethyl 9-decenamide (Steposol MET 10U, Stepan Co., Northfield, Ill.) induces substantial thinning of the system. Other exemplary solvents, including but not limited to Hexyl Carbitol™ (Dow Chemical Co., Midland, Mich.), polypropylene glycol-10 cetyl ether (Procetyl 10, Croda Inc., Edison, N.J.) and phenoxyethanol (Dowanol Eph, Dow Chemical Co., Midland, Mich.), disperse uniformly without substantially affecting system viscosity, but produce a strongly hazy opaque system. Other solvents, including but not limited to methyl esters of fatty acids (Stepanol C-25, C-40, C-48, C65, Stepan Co., Northfield, Ill.), produce similarly opaque dispersions but require a surfactant such as polysorbate-20 (Ritabate 20, Rita Corp., Crystal Lake, Ill.) to form a fine dispersion.

Yet other organic solvents form clear solutions without substantially altering the rheological properties of the suspending systems of the present invention. These may for example be incorporated into the gel beads of Example 4 by pre-dissolving or dispersing the solvents in the alginate solution in place of the argan oil payload, with or without surfactant as needed to disperse the solvent phase.

Non-limiting examples of solvents that may be included in such compositions include 2,2-dimethyl-4-hydroxymethyl-1,3-dioxolane, (Augeo Clean Multi, Rhodia S. A., La Défense, France), tripropylene glycol methyl ether (DOWANOL™ TPM glycol ether, Dow Chemical Co., Midland, Mich.), propylene glycol Mono-n-propyl ether (DOWANOL™ PNP glycol ether, Dow Chemical Co., Midland, Mich.), PPG-2 propyl ether (DOWANOL™ PNP glycol ether, Dow Chemical Co., Midland, Mich.), propylene glycol methyl ether (DOWANOL™ PM glycol ether, Dow Chemical Co., Midland, Mich.), PPG-2 methyl ether (DOWANOL™ DPM glycol ether, Dow Chemical Co., Midland, Mich.), propylene carbonate (Jeffsol propylene carbonate, Huntsman Corp., The Woodlands, Tex.), ethyl lactate (PURASOLV EL, Corbion Corp. Lenexa, Kans.), short chain water soluble alcohols such as methanol, ethanol, isopropanol, glycerin, 1,3 propanediol (Zemea®, DuPont Tate & Lyle Bio Products Co, LLC, Loudon, Tenn.), and similar materials.

EXAMPLES

In some aspects, the invention provides a method of making shear-thinning aqueous rheological systems. The method comprises combining an aqueous solution of alginic acid and/or its salts with an aqueous solution of an extract of *Aloe vera* and/or any of a variety of succulents.

In some aspects, the invention provides a product comprising a pseudoplastic or shear-thinning aqueous rheological system. The rheology of the system is dependent upon the concentration of each of the components, but systems capable of suspending bubbles or particles are readily formed. Systems with the gel strength required to suspend particles may be formed, yet these same systems are nonetheless sufficiently shear-thinning that they can be dispensed as an atomized mist using a standard finger-pump, triggerspray commercial dispenser, or to pass easily through a self-foamer commercial dispenser.

In some aspects, the invention provides a sprayable product that deposits a film that is resistant to dripping, running, or spreading.

Example 1

Formation of a Shear-Thinning Rheological System of Sodium Alginate and *Aloe vera* Extract An aqueous solution, A, comprising 20 mL of 1.0% wt. sodium alginate (Manucol® DH, FMC Health & Nutrition, Philadelphia, Pa.) was prepared, and adjusted to pH 5 if needed, by addition of, for example, trace citric acid (Spectrum Chemicals, New Brunswick, N.J.). A second aqueous solution, B, comprising 20 mL of 1.0% wt. *Aloe vera* powder (100% Organic *Aloe Vera* Whole Leaf Powder 200X, Earth Supplied Products, Naples, Fla.) was added to solution A while it was stirred at 700 rpm. Within seconds of addition, the combined solution thickened dramatically, and if stirring was stopped, entrained bubbles were seen to be immobilized in a gel-like fluid. The fluid may be cooled to freezing or heated to 80° C. or above without loss of this suspending quality. Despite this gel-like consistency, the fluid was readily sprayed using a common dip-tube fingerpump cosmetic atomizer or trigger sprayer, and the spray pattern was very similar to that of water alone. While the spray pattern reflected extreme viscosity loss while under shear conditions, the deposition of material from the spray cone showed recovery of viscosity, and repeated sprays built up a layer of material on a vertical surface that did not spontaneously flow under gravity until a substantial accumulation had occurred, for example, more than 2 mm thickness. The impact of individual arriving droplets was apparently insufficient to de-gelify the accumulated layer, thus allowing thickness to build. The fluid had mild if any flavor and aroma, and the mouth feel was innocuous. The skin feel of the fluid was very pleasant, with good slip. As the fluid evaporated to dryness, there was a brief period of mildly tacky feel, but this rapidly dissipated to a soft, moisturized skin texture. The material does not "pill" or form gross aggregates when rubbed during drying. Virtually identical systems resulted if the *Aloe vera* solution was substituted with extracts from the leaves of *Crassula ovata*, a common ornamental often known as "Jade plant" or from the leaves of *Carpobrotus edulis*, a low, spreading decorative plant often known as "Ice plant" or similarly from any of a variety of plants of the identified families.

In another aspect the invention provides a product with visible droplets or particles in suspension, that is nonetheless readily atomizable with a finger-pump or trigger sprayer and passes easily through a self-foamer.

Example 2

Moisturizing Product with Visible Suspended Droplets

To the system formed in Example 1, above, 0.5 mL polydimethylsiloxane (SPI 350, Silicones Plus, Arlington, Tex.) was added and stirred at 700 rpm. In the absence of an emulsifying agent, the silicone phase broke into mm scale, attractive clear droplets. Upon cessation of stirring the dispersed droplets remained suspended, showing no evidence of movement after one week at 50 C. The suspension was fully atomizable through a common finger-pump atomizer, and no silicone droplets were distinguishable in the product after passing through the sprayer, which apparently effectively emulsified the product. The product had a good cosmetic feel, with moisturizing benefits from the *Aloe* and alginate components and characteristic smoothness and slip of silicone. Alternatively, a material to be suspended may be first dispersed in the alginate solution, and then the *Aloe* may be subsequently introduced to generate the final rheological properties of the system.

In another aspect, the invention provides a method of making aqueous gelled particles. The method comprises introducing droplets of an aqueous precursor liquid comprising alginic acid and/or its salts into a curing bath comprising at least one succulent extract.

Example 3

Formation of Aqueous Gelled Particles

An aqueous solution A of 1% wt. sodium alginate was added dropwise to a bath B of a 5% wt. aqueous solution of *Aloe vera* powder. As droplets entered the bath, they rapidly cured to form discrete rigid, clear gel particles. The particles could be harvested by passing the bath through an appropriately sized screen. There is no apparent limit to the size of particles produced by this method, although large particles may not gel on the interior, or may do so impracticably slowly. However, particles from about 20 µm to about 1 cm were readily formed by dropping or spraying solution A into the bath. Smaller or larger particles may be produced according to methods well known in the art of producing gelled particles from other polymer systems. These particles, like the suspension system of Example 1 were not unpleasant in taste or odor. Virtually identical particles may be produced by substituting the juice pressed from fresh *Carpobrotus edulis* leaf and stem material for the 5% *Aloe* solution.

In another aspect, the invention provides a method of forming aqueous gelled particles containing additional payload material suspended, emulsified or otherwise dispersed such that the resulting gelled particles entrap or encapsulate the additional payload material.

Example 4

Formation of Aqueous Gelled Particles Containing a Payload

The aqueous solution A of Example 3, above, was modified by diluting by 25% wt. with a 1% aqueous solution of carrageenan (Viscarin® PC 209, FMC Health & Nutrition, Philadelphia, Pa.) and further by dispersing in the resulting solution argan oil (*Argania spinosa* oil, Earth Supplied Products, LLC, Naples, Fla.) at 1% wt with lauryl glucoside (Pureact Gluco L, Innospec Inc., Englewood, Colo.) at 0.005% wt. to form an emulsion of the oil within phase A. The resulting emulsion was added dropwise to the bath as in Example 3, above. The particles thus formed included argan oil droplets entrapped within each bead, and compressing or shearing the beads released the oil. Dilution of the alginate solution with a solution of an additional polymer that does not interact synergistically with *Aloe*, for example a solution of 1% sodium carboxymethylcellulose (Akucell AF 1985, AkzoNobel, The Netherlands) reduced the gel strength of the beads such that they were more readily crushed or sheared. Viscarin® PC 209 carrageenan (FMC Health & Nutrition, Philadelphia, Pa.) is another example of such a non-gelling polymer.

In another aspect the invention provides a product comprising a shear-thinning suspending agent comprising an aqueous solution of alginic acid and/or its salts and at least one succulent extract, further comprising a suspension of gelled particles formed as described above.

Example 5

Suspension of Aqueous Gelled Particles

The beads of examples 3 and 4 were further suspended in the system of Example 1, above, and because of the emulsified oil phase, the beads of Example 4 were particularly visible in the clear suspension. In particular the beads of Example 4 were more subject to disruption because of reduced gel strength. Such beads formed at an appropriate size were able to travel with the suspending phase through the dip tube of a pump atomizer and shear open during spraying. The fineness of the resulting mist was apparently unaffected by the beads.

In another aspect the invention provides a method of forming cast gels.

Example 6

Cast Aqueous Gels

An open-topped molding form was filled with the 5% aqueous *Aloe* bath solution of Example 3. Solution A of Example 3 was poured or otherwise dispensed into the form, displacing the bath solution. Solution A began to gel as it was introduced to the form, but when solution A had fully filled the form, displacing the bath solution, the entire form was further immersed in additional bath solution. (Alternatively, the bath solution may be "basted" over the surface of solution A to hasten gelation.) After several minutes solution A formed a firm gel and could be removed from the form. It was also possible to partially dry the solution in place to form a more rigid gel before removal. If the form was sufficiently thin, such as for a gel sheet or film, gelation could be accomplished by contact on only one surface of solution A by the bath solution.

Alternatively, a form or mold may be filled with the synergistic rheology fluid formed by combining, in a manner similar to Example 1, a 2% solution of sodium alginate with an equal volume of a 1.5% aqueous *Aloe* solution. The aqueous portion of the fluid is permitted to evaporate, which may be assisted by heating or accelerated air exchange. As the solution concentrates through evaporative loss, the gel threshold is passed, and the material solidifies irreversibly to a firm gel that will not redissolve to a dilutable product, but rather remains a gelled solid even in the presence of additional water. As the gelation and drying of the surface slows the transport of water from deeper layers, for larger volumes of material, the method may accelerated by repeated casting of a thinner film in multiple cycles. Each thin film is cast upon the previous, accreting more material with each layer until the mold is fully filled.

In another aspect the invention provides a product comprising aqueous gelled materials further comprising a drug.

Example 7

Ibuprofen Loaded Aqueous Gel Particles

In this example a rheologically synergistic fluid was prepared, which was used to suspend a particulate drug material. Drops of this suspension were introduced to a bath to produce gelled beads. An aqueous solution A of 9 g containing 2% wt sodium alginate was prepared. A second aqueous solution, B, containing 9 g of 1% aqueous *Aloe* solution was prepared separately, then added to solution A. A 2 g sample of ibuprofen was dispersed into the combined aqueous solution by stirring. The ibuprofen remained suspended in the alginate/*Aloe* system, and continued mixing was not necessary to retain homogeneity of the drug dispersion. The bath solution of Example 3 was prepared, and to the bath was added additional ibuprofen at 50 mg/L, in excess of the aqueous solubility of the drug, to preclude leaching of the drug out of the particles. The drug dispersion thus prepared was introduced dropwise into the bath, thus forming beads containing approximately 10% ibuprofen by weight.

In another aspect the invention provides a product comprising aqueous gelled materials further comprising a flavorant.

Example 8

Aqueous Gel Beads Comprising Mint Flavor

The method of Example 4 was reproduced, substituting peppermint oil (Spectrum Chemicals, New Brunswick, N.J.) for argan oil, to produce aqueous gel beads. Because the oil has limited water solubility, the beads thus formed had a mild minty flavor unless broken open. Applying shear force to the beads released the oil emulsified therein, resulting in a localized burst of flavor.

In another aspect the invention provides a product comprising aqueous gelled materials further comprising a colorant agent.

Example 9

Aqueous Gel Beads Comprising a Pigment

The beads of Example 7 were prepared, substituting 0.5 g gold pigment (Ronastar® Gold, EMD Chemicals/Rona, Savannah, Ga.) for the 5 g sample of ibuprofen. As the pigment was not water-soluble, the beads thus formed retained their color and would not leach into a suspending medium.

In another aspect the invention provides a product comprising aqueous gelled materials further comprising a colorant agent and a flavorant.

Example 10

Aqueous Gel Beads Comprising Mint Flavoring with a Colorant

The product of Example 8 was reproduced, except that prior to dispersion of the peppermint oil phase, a lipophilic dye (D&C Green #6, Spectrum Chemicals, New Brunswick, N.J.) was dissolved in the oil. As the dye was water-insoluble, the beads thus formed would not leach color into an aqueous system.

In another aspect the invention provides a product comprising aqueous gelled materials further comprising a fragrance.

Example 11

Aqueous Gel Beads Comprising a Fragrance Material

The product of Example 4 was reproduced, substituting lavender oil (Spectrum Chemicals, New Brunswick, N.J.) for argan oil, to produce aqueous gel beads. As the oil has limited water solubility, the beads thus formed possess a moderately strong lavender aroma unless sheared. Applying shear force to the beads caused release of the fragrance oil emulsified therein. As the beads are easily sheared, fragrance can be released by dispensing the suspended beads as a mist or in a foaming soap product. In another aspect the invention provides a product comprising aqueous gelled materials further comprising an oral health benefit agent.

Example 12

Aqueous Gel Beads Comprising an Oral Health Benefit Agent and a Flavor

The product of Example 8 was reproduced, but before dispersing the peppermint oil phase a 5% wt aliquot of an aqueous solution of 0.1% sodium fluoride (Sigma-Aldrich, St. Louis, Mo.) was dispersed in the oil phase using 0.5% wt sorbitan monooleate (Jeechem SMO, Jeen Intl. Corp., Fairfield, N.J.), to form a water-in-oil emulsion. As this emulsion was dispersed into the alginate solution, A, it formed a water-in-oil-in-water emulsion, retaining the majority of the sodium fluoride within the oil droplets. This would inhibit incompatible chemical interaction with other components, for instance in a dentifrice composition, until release of the fluoride component by shear.

In another aspect the invention provides a product comprising aqueous gelled materials further comprising a skin and/or hair benefit agent.

Example 13

Aqueous Gel Beads Comprising a Skin and Hair Benefit Agent

The product of Example 4 was reproduced, but the argan benefit oil was replaced with shea (*Vitellaria paradoxa*) oil (Shea Olein, Earth Supplied Products, Naples, Fla.) The skin feel of the resulting product was similar to that of Example 4. When the product was sprayed onto hair, an immediate increase in softness and reduced resistance to combing was produced.

In another aspect the invention provides aqueous gelled materials further comprising an industrial or household benefit agent.

Example 14

Aqueous Gel Beads Comprising a Home Care Benefit Agent

The product of Example 4 was reproduced, but the argan benefit oil and surfactant were replaced by a 10% aqueous solution of lauryl glucoside. The resultant beads released surfactant when sprayed upon a surface, or when poured upon a surface and rubbed as a cleaning agent.

Products according to the invention may comprise two or more populations of aqueous gelled materials, each population including a different payload material that needs to be protected against premature interaction with the payload material in the other. Similarly, materials confined within a single population of beads may be protected against interaction, or premature interaction, with components in the continuous phase or external environment. For instance, chemically incompatible materials maybe kept apart in this way. For example, gelled particles containing an opaque emulsion of an immiscible cleaning solvent, such as limonene, contribute both the benefit of the cleaning solvent and an appealing visual appearance as discrete beads in a clear surfactant base, which may be desirable as visually distinct from a simple continuous whitish emulsion product, conferring novelty and connoting modernity and efficacy in a consumer cleaning product. Such a product would additionally minimize contact between the solvent component and the packaging during extended storage, reducing the potential for undesired product/packaging interactions such as leaching of plasticizers or package discoloration or failure resulting from solvent replasticization of the container.

One or more such bead or particle populations may be suspended to form a product comprising beads with multiple colors or payloads. For example two populations of beads containing materials that are desired to be segregated until dispensed could be co-suspended so as to prevent interaction until the product was dispensed. For instance, an enzyme payload in one bead population could be isolated from a ZnO sunscreen agent in another population.

Alternatively, multiple payloads may be combined in the same bead. By combining multiple payloads in the same bead, as by combining fragrance and pigment or colorant in the same bead, a simple means of product customization can be realized wherein the same surfactant base might be used with different color/fragrance bead populations to produce visually distinct finished products with different fragrances.

Example 15

Populations of Aqueous Gel Beads Comprising Different Materials that React When Brought into Contact The product of Example 4 was reproduced to form a population of beads, A, but the argan benefit oil and surfactant were replaced by a 0.5% aqueous triethanolamine (Spectrum Chemicals, New Brunswick, N.J.) solution with an additional 0.5% of an indicator dye (phenol red, Spectrum Chemical, New Brunswick, N.J.). A second population of beads, B, was made in the same manner, but substituting a 1% citric acid (Spectrum Chemical, New Brunswick, N.J.) solution for the argan oil. As formed, population A was yellow, while population B was clear. If the two populations were brought into contact or sheared together, the resulting acidification of the indicator dye turned the population A beads bright red. Such systems of interacting bead populations may be incorporated into sensors, visual indicators, etc. according to methods known to those skilled in sensor design.

In another aspect the invention provides a product comprising aqueous gelled materials further comprising a dietary supplement or a vitamin.

Example 16

Aqueous Gel Beads Comprising a Nutritional Supplement

The product of Example 4 was reproduced, but the argan benefit oil was replaced by fish oil. The resultant product effectively masked the flavor of the fish oil.

In another aspect the invention provides a product comprising aqueous gelled materials further comprising live organisms, probiotics, or prebiotics.

Example 17

Aqueous Gelled Materials Comprising Live Organisms or Probiotics

The method of Example 3 was reproduced, but prior to adding to the bath, a live culture of microorganisms found in kefir grains and used in beverage manufacture was dispersed into solution A. Solution A may be further modified to include inulin (Oliggo-Fiber™ Inulin, Cargill Industries, Wayzata, Minn.) or other pre-biotic materials capable of supporting beneficial gut flora.

In another aspect the invention provides a product comprising a suspension of aqueous gelled materials for application to skin or hair.

Example 18

Sprayable Product Comprising a Shear-Thinning Rheological Fluid Further Comprising Aqueous Gelled Materials for Application to Skin or Hair The product of Example 13 was reproduced and suspended in the shear-thinning composition of Example 1. The resulting combination product was sprayable as an atomized mist, and the particles did not negatively impact sprayability. When the product was applied as a liquid, for instance upon skin, the feel was cosmetically pleasant and mildly emollient. The tack phase or brief period of adhesive feel during drying was counteracted by the benefit oil. When the product was applied to hair as a spray, the hair became immediately softer and combing resistance was reduced. The product further acted as a detangler and reduced frizz.

In another aspect the invention provides a product comprising a suspension of aqueous gelled materials for ingestion as a food or beverage.

Example 19

Product Comprising a Suspension of Aqueous Gelled Materials for Ingestion as a Food or Beverage The product of Example 13 was reproduced, but with the inclusion of 0.2% of a ginger flavor concentrate (Ginger Flavor Wonf, Natural Organic NOP, A.M. Todd Botanical Therapeutics, Smithfield, Utah), to form a flavored beverage including the rheological system previously described. The gelled materials of Example 4 were reproduced, replacing the argan oil and surfactant with lemon flavor (Lemon Extract, Natural Organic NOP, A.M. Todd Botanical Therapeutics, Smithfield, Utah) in phase A, such that the resultant aqueous gel particles entrapped lemon flavor within the particles. The two products thus formed were combined, such that the particles were suspended in the beverage, forming a drink that resisted sedimentation of the suspended particles. By adjusting the concentration of the *Aloe* and alginate components of the rheological suspending system, it is possible to suspend larger particles or pieces of fruit, with or without forming encapsulating particles surrounding them.

In another aspect the invention provides a product comprising aqueous gelled materials further comprising components that may be modified by heating or cooking.

Example 20

Product Comprising Aqueous Gelled Materials Further Comprising Components that May be Modified by Heating or Cooking The product of Example 4 is reproduced, but the argan oil and surfactant are excluded, and in their place, 25% wt raw egg or an equivalent quantity of a 5% wt solution of ovalbumin (Sigma-Aldrich, St. Louis, Mo.) is blended with the other components of solution A prior to formation of particles. The particles thus formed may be modified by heating to form a cooked or thermally denatured product.

In another aspect the invention provides a product for application to a surface, which may comprise aqueous gelled materials further comprising an abrasive or polishing agent.

Example 21

Product Comprising a Suspension of Aqueous Gelled Materials Further Comprising a Surfactant and Further Comprising Aqueous Gelled Materials Further Comprising an Abrasive or Polishing Agent The product of Example 13 was reproduced, but with the inclusion of a cleaning surfactant, for instance 3% wt lauryl glucoside (Plantaren® 1200 N UP, BASF, Germany) to form a cleaning solution including the rheological system previously described. The gelled materials of Example 4 were reproduced, but the argan oil and surfactant were replaced by an abrasive or polishing agent in phase A, 0.5% wt fine pumice (volcano powder, Earth Supplied Products, Naples, Fla.) such that the resultant aqueous gel particles entrapped abrasive particles. The two products thus formed were combined, such that the particles were suspended in the stock, forming a sprayable surfactant that resisted sedimentation of the suspended particles. When the product was sprayed, the abrasive particles were distributed upon the surface along with the surfactant. The abrasive retained a thin coating of the gel phase, and if the product was gently wiped away, limited abrasion resulted. If the product was scrubbed more vigorously, as to remove a stain, more abrasive was liberated, strengthening the scouring activity of the product.

In another aspect the invention provides a product comprising aqueous gelled materials that have been subsequently dried.

Example 22

Method of Forming Rehydratable Dried Gel Particles and Product Thereof

The product of Example 9 was reproduced, with the addition of 1% wt glycerin. The resulting beads were washed in a 70% ethanol/water solution to dehydrate the exterior, and then dispersed over a support surface (glass or Teflon) in a uniform layer and dried under a 50° C. airflow until hardened. The resulting particles were scraped from the support surface and collected. The product thus formed was able to rehydrate when placed in water to produce discrete particles. The particles thus formed retained the pigment payload through the process of drying and rehydration. During rehydration the particles swelled to a size and shape similar to the original particles, and after rehydration they similarly released payload under shear conditions. In the dehydrated state, however, the particles were much less shear sensitive and were able to be mixed vigorously or pumped without releasing the payload. A fairly complete dehydration was accomplished by the above-described method, but use of lower temperatures and/or shorter times can produce partially dehydrated particles, which are less firm and rehydrate more quickly.

Example 23

Method of Forming Rehydratable Dried Gel Films and Product Thereof

A 20 mL aliquot of an aqueous solution comprising 14.5 mL of 1.5% wt. sodium alginate, 4 mL of a 1% aqueous solution of a non-gelling carrageenan similar to that of Example 4, and 0.5 mL of glycerin was combined with a 15 mL aliquot of 1.5% wt aqueous *Aloe* solution to form a synergistic rheological fluid. The fluid was cast as a 4 mm thick sheet and dried under a 50° C. airflow until a tough, peelable film was formed. The film, though dry was resilient and flexible. Upon immersion in water or an aqueous solution, the film rehydrates to form a soft, elastic gel that adheres to many surfaces, for instance, metal, plastic, or skin, on contact. While the gel was flexible and deformable, it was sufficiently strong to survive repeated adhesion/peeling cycles without tearing. Thinner or thicker sheets can be produced by using the same method but forming an initial layer of different thickness, or casting multiple layers before fully drying.

In another aspect the invention provides a product comprising aqueous gelled materials that have been subsequently dried and then rehydrated with a solution comprising water, which may also comprise additional agents.

Example 24

Rehydratable Film Product for Application to Skin

The cast gel product of Example 23 was produced in a customized shape to fit a body part, in this case a human face. The mask was dried into a planar film on a backing sheet for convenient packaging. The dried film was rehydrated in a "tea" of beneficial agents, which in this case included herbs and plant extracts. Following rehydration, such a film may be applied to the skin, such as the user's face, and left in place to partially dry. The skin is afforded the benefit of the cooling evaporation, the herb tea, and the *Aloe*/alginate components. Further after partial drying, the mask becomes adherent and peels off, providing further exfoliation benefit, and potentially removing toxins or waste products from the surface of the skin. The films of this example may be cast in a selected shape or cast as sheets and cut to shape after drying.

In another aspect the invention provides a product comprising a sweetened flavored cast gel, that further comprise a benefit agent, for example a vitamin.

Example 25

Method of Forming a Sweetened, Flavored Cast Gel, that Further Comprises a Benefit Agent, for Example A Vitamin, and Product Thereof The method and materials of Example 22 are reproduced, but a vitamin, for example cobalamin, also known as vitamin B12, a flavor, for example orange flavor (Orange Flavor, Natural Organic NOP, A.M. Todd Botanical Therapeutics, Smithfield, Utah), and a sweetener, for example sugar, are dissolved or dispersed into the solution before casting. The solution is poured into a mold and dried to a firm, chewy texture.

Alternatively, the gel can be dried completely to form a blank, loadable unit. The unit can then be partially rehydrated by immersion in an aqueous solution of the desired materials, and is thereby charged with the payload. The resulting loaded product can be further dried or used as formed.

In another aspect the invention provides a product comprising gel particles further comprising an irritant substance such that risk of accidental exposure was reduced.

Example 26

Product Comprising Gel Particles Further Comprising an Irritant

The method of Example 3 was reproduced, but solution A was modified by dispersing 5% wt of a 5% solution of capsaicin (Spectrum Chemicals, New Brunswick, N.J.) in capric/caprylic triglycerides (PELEMOL® CCT, Phoenix Chemical, Somerville, N.J.) prior to introduction to the curing bath. The resulting particles could be further stabilized by drying. The entrapped material was thereby encased in a protective bead structure until released by shear and/or hydration.

In another aspect the invention provides a method of forming a gel film in situ on a surface, and the product thus formed, which may further comprise a benefit agent.

Example 27

Method for In Situ Formation of a Gel Film, and Product Thereof

A solution of the synergistic rheology fluid of Example 1 was sprayed or otherwise dispensed on a surface, for example a wounded or damaged site in skin, to form a layer approximately 1-3 mm thick. A 5% wt aqueous *Aloe* solution was sprayed or otherwise dispensed over the alginate solution, curing it in place to form a gel film. If open to air, the film dried superficially, providing sustained cooling and forming a barrier to foreign material entering the area of compromised skin barrier. Such a synergistic rheology fluid could be modified to comprise a benefit agent, for example an antimicrobial agent, for example, 0.5% wt silver nitrate (Spectrum Chemicals, New Brunswick, N.J.) and/or an analgesic, for example 0.1% wt benzocaine HCl (Spectrum Chemicals, New Brunswick, N.J.).

In another aspect the invention provides a product comprising a surface film resistant to dissolution.

Example 28

Method of Forming a Water Resistant Topical Film and Product Thereof

The synergistic rheological system of Example 1 is sprayed onto a surface, for example, skin. As the system dries and becomes more concentrated, a firm gel is formed. Once the gel state is reached, the film becomes substantially resistant to removal by water alone. Further drying increases the rinse resistance of the film. Depending upon the thickness of the layer sprayed, the film may be distinct and peelable, or if thinner may be almost imperceptible. If an additional component is included, for example a component that interacts with light, for instance a sunscreen, a dye or a visible pigment, the rinse-resistance of the resulting dispersion is readily observed.

In another aspect the invention provides a product comprising cast gels that further contain dispersed visible particles.

Example 29

Cast Gel Films with Included Gel Particles

The rheological system used for the cast gel film of Example 23 is reproduced, and the particles of Example 22 are dispersed in that solution. This product is subjected to the same processing as in Example 23 to produce a film with inclusions of the gel particles of Example 22. These particles may be made so as to be visually distinct or to deliver a benefit agent separate from any benefit agent included in the bulk of the cast film.

Example 30

Method of Forming a Protective Gel Film Around an Object

A carrot or sliced apple was coated with a solution comprising 1% aqueous sodium alginate solution, by spraying or dipping. The coated object was then further coated with a 1% wt aqueous *Aloe* solution. The resulting gel film impeded water loss without contributing an undesirable texture, flavor, or appearance. Alternatively, a synergistic rheological fluid such as the product of Example 1 could be used to coat the object in a single step.

Example 31

Method of Forming a Re-Dissolvable Precipitate Comprising Alginic Acid and/or its Salts and a Succulent Extract and the Product thus Formed A 100 mL aliquot of the synergistic rheological system of Example 1 was modified by the addition of 0.5% wt glycerin and 1% wt sodium chloride. The resulting solution was introduced to a roughly equal volume of 95% aqueous ethanol solution. The ethanol may be added to the aqueous system or vice versa, and the process may be performed gradually or abruptly. The polymer solution formed a stringy precipitate as it was introduced to the full volume of ethanol solution. This mass could be harvested by filtration, and further ethanolic bath solution could be removed by applying pressure to the material or pulling air through it using a Buchner funnel apparatus. The resulting partially dehydrated material was readily re-dissolved by adding as a mass to a stirring volume of water, and the resulting solution was essentially identical to the initial solution. Importantly this product was not fully dried, but remained a partially hydrated gel.

In another aspect the invention provides a method of forming a re-dissolvable concentrate comprising alginic acid and/or its salts and a succulent extract and further comprising suspended material, and the product thereof.

Example 32

Re-Dissolvable Product Concentrate Comprising Alginic Acid and/or its Salts and a Succulent Extract and Further Comprising Suspended Material The method of Example 31 is applied to a synergistic rheological system similar to solution A of that example, but solution A additionally comprises material in suspension. For instance, solution A may further comprise the blue mint gel beads of Example 10 and a vanilla flavorant, or it can comprise the fish oil gel beads and an orange juice concentrate in the suspension. The resultant partially dehydrated precipitate formed by the method of Example 31 entraps these suspended materials. Upon re-dissolution, the original rheology is restored, and the materials are suspended anew to form a complete formulated product.

In another aspect the invention provides a product comprising aqueous gel beads further comprising a sunblock agent.

Example 33

Zinc Oxide Loaded Particles

The method of Example 4 was reproduced, replacing the argan oil component with a dispersion of 1% wt hydrophobically modified zinc oxide (Zano 10, Ultra Chemicals, Red Bank, N.J.) in 5% wt eicosane (Permethyl 102A, Presperse Corp, Somerset, N.J.). The resulting multiphase dispersion was processed as described in Example 4. The resulting particles contained droplets of eicosane, within which were dispersed particles of zinc oxide. Such visibly distinct and readily shearable particles may further provide a novel and entertaining format for sunscreen application for children.

In another aspect the invention provides a reversibly gelling composition suitable as an environmentally-friendly suspending agent for use in oilfield applications, for example hydraulic fracturing methods or "fracking".

Example 34

Reversible Gelation Method and Product Suitable as an Environmentally-Friendly Suspending Agent for Use in Oilfield Applications, for Example Fracking The synergistic rheological system of Example 1 was reproduced, and further a 10% wt loading of sub-millimeter scale quartz sand, as is commonly used as a "proppant" in hydraulic fracturing, was dispersed so as to be suspended in the system. The system maintained this material in a stable suspension. The system could be destabilized by addition of 2% sodium chloride, or acids or bases sufficient to shift the pH to 2 or 12, respectively, to reverse the synergistic gelation effect.

In another aspect the invention provides a product comprising a suspension of aqueous lightly gelled materials and/or microbeads for application as a nasal spray.

Example 35

Product Comprising a Synergistic Rheological System Further Comprising Dissolved or Suspended Materials for Application as a Nasal Spray The synergistic rheological system of Example 1 is reproduced, and this system is modified by addition of preservative [for example Euxyl K 712 Shülke & Mayr, Germany] and a suitable fragrance. The resultant system is sprayable and provides a non-drip base for a nasal spray. The system may be further modified by inclusion of any of a variety of medicaments suitable for treatment of disease symptoms, for example a steroid or an adrenergic agonist.

In another aspect the invention provides a method of producing fibers and the resulting product.

Example 36

Method of Producing Fibers and Resulting Product

A 1% aqueous solution, A, comprising sodium alginate was forced through a 27 gauge hypodermic needle that was submerged in a bath comprising 5% *Aloe* extract. The alginate was introduced with sufficient pressure, about 5 psi, such that the flow separated from the needle tip rather than pooling locally. The resulting stream of alginate gelled as it was extruded into the bath to form a continuous fiber. The fiber could be harvested by filtration, or could be withdrawn continuously from the bath on a screen support. The resulting dried fibers from this model system were approximately 100-200 μm radius and circular in cross section. Use of smaller and larger gauge needles to provide different sized orifices, produce smaller and larger fiber dimensions and correspondingly change the rate of deliver of material into the bath. Benefit agents, non-limiting examples of which include flavors, drugs or antimicrobials, can be included in solution A to be pre-loaded in the fibers, or they can be loaded by rehydrating the fiber in an aqueous solution of those materials. The fiber produced above was not negatively affected by multiple cycles of drying and loading. Solution A can further comprise a dispersed fragrance at 1% wt, similar to Example 11 and thus the fragrance is entrapped. After drying, the such fibers thus formed do not emit a strong odor, but on rehydration, the fragrance becomes strong and noticeable. In a manner similar to Example 10, solution A may further comprise a colorant, and the color imparted to the fiber intensifies upon drying.

In another aspect the invention provides a method of analyzing the purity of a sample of a succulent extract.

Example 37

Method of Determining the Purity of a Succulent Material Extract

A 0.5% solids aqueous solution of the succulent extract, for example *Aloe vera* powder concentrate, is prepared as the sample to be tested. A 5 mL aliquot of this solution is combined with a 10 mL aliquot of a 1% aqueous sodium alginate solution at pH 5. The viscosity of the resulting solution is compared to the viscosity of a similar combined solution made with a known standard sample of the succulent extract. If the viscosity of the unknown sample is lower, the purity of the extract is questionable. A standard curve can be produced by measuring the quantity of a known sample solution of varied concentrations required to reach a particular viscosity target when combined with the acidified alginate. Sample purity of an unknown can be analyzed quantitatively by finding the corresponding concentration required to develop the same target viscosity in the alginate system. The test does not establish the identity of the unknown sample, however. If the required concentration of the sample matches the standard, the sample could contain a different succulent extract. However, this method can reliably identify samples that contain material that is not derived from the active portions of the succulent plant. For instance, if an *Aloe* leaf extract contains material that has been adulterated with a filler material, such a sample can be readily identified by the above-described method. Further the method is essentially instantaneous, requires minimal equipment, and the small volumes of test solutions can be pre-prepared and taken to the field. With appropriate preservation, for example with 0.1% Euxyl K100, (benzyl alcohol methylchloroisothiazolinone, and methylisothiazolinone, Schülke & Mayr GmbH, Germany), the test solutions can be stored at ambient temperature for many months, and potentially much longer without losing potency.

In another aspect, the invention provides a method of making aqueous gelled particles comprising introducing droplets of an aqueous liquid comprising at least one succulent extract into a bath comprising alginic acid and/or its salts.

Example 38

Method of Forming Aqueous Gel Particles Enriched in a Succulent Extract

The method of Example 3 was followed; however in this case the aqueous solution A comprising 1% sodium alginate was used as the bath, and the aqueous solution B comprising 5% wt. aqueous *Aloe* solution was added dropwise to that bath. The resultant particles formed initially with a distinct skin of gelled *Aloe*/alginate. If harvested from the bath rapidly, a liquid *Aloe* solution core was retained in the particles. If the particles were permitted more curing time in the bath, they eventually gelled throughout, at a rate depending upon particle size. For example, 5 mm droplets took several minutes to gel completely at room temperature. Without being bound to a particular understanding, it is possible that the more viscous alginate solution diffuses into the particle much more slowly than the *Aloe* components do in the case where the alginate forms the droplet interior.

In another aspect the invention provides dry, rehydratable particles that may further comprise benefit agents, for example a fragrance, and may be useful as an antiperspirant.

Example 39

Water Absorbing, Non-Dissolving Powder

The composition of Example 1 was completely dried and the resulting material was ground to form a powder. The grains of the powder were rehydratable yet water-insoluble, and individually absorbed water to swell and form gel particles. The powder applied to skin provides a water-absorbing function and an occlusive function, useful in combating excessive perspiration. The powder may be applied as is or may be used as an ingredient dispersed in a formulated composition.

Example 40

Microstructured Fluid

In another aspect the invention provides a microstructured fluid containing regions of higher and lower gel strengths respectively, such that some regions remain largely gelled while others exhibit shear-thinning liquefaction. An aqueous solution, A, comprising 20 mL of 5.0% wt. sodium alginate was prepared at pH 5. A second aqueous solution, B, comprising 2 mL of 5.0% wt. *Aloe vera* powder was added dropwise to solution A, stirring at 1000 rpm. The concentrated *Aloe* solution induces inhomogeneous, localized gelation of small regions of the alginate solution, but upon completion of the addition, the bulk material exhibits rheology similar to that of example 1. A benefit agent may be included in solution A prior to gelation, for example a fragrance oil. Microscopic examination of a thin layer of the product reveals lumpy, irregular blobs ranging from tens to several hundreds of microns across, entrapping a fraction of the dispersed benefit agent. If the material was diluted, these blobs persisted, while the less firmly gelled interstitial material was diluted and thinned. Those familiar with producing polysaccharide gels will be aware that the scale of the gelled particles may be manipulated by altering the shear force, addition rate, concentration, and/or viscosity of the either solution component. Surprisingly, the gelled regions of the product thus formed exhibited good deposition onto clothing fabric when in dilute suspension. Without being bound to any particular interpretation, a fraction of the particles appear to be of an appropriate dimension to be caught in the fabric structure, as fish may be entangled in a net, and the irregular shape and elastic texture of the gelled particles may assist in their entanglement as they are wedged into the mesh. The result of this deposition was that a fragrance entrapped or encapsulated by the gelled particles was noticeably transferred onto fabric in excess of an equivalent quantity of free fragrance. This wet deposition was effective in the context of surfactants and laundry detergents, providing enhancement of fragrance delivered for instance upon removing damp fabric from a washing machine.

It will be apparent to the person skilled in polysaccharide gel technology that materials may be prepared as in any of the above aspects so as to combine more than one of these qualities in a single population of materials.

Example 41

Topical Moisturizing Composition Containing Glycerin

The composition of Example 1 was reproduced, with further inclusion of 0.5% glycerin (ESP Organic Glycerin, Earth Supplied Products, Naples, Fla.). (The glycerin component is readily water soluble and can be added to either the alginate or the *Aloe* solution components, or can be added after formation of the synergistic system.) The resulting product provided an additional moisturizing benefit and reduced the tacky skin feel associated with topically applied glycerin. This variant of the composition of Example 1 may be further substituted for that product in subsequent examples, as in Example 2 and Example 5 to extend the moisturizing benefit of included glycerin to those products.

Example 42

Topical Moisturizing Composition Containing Glycerin and Antioxidants in a Water-in-Oil Dispersion wherein the Synergistic Gel Composition is Present as a Dispersed Phase The composition of Example 1 was reproduced, with further inclusion of 0.5% glycerin and 2% Green Coffee Antioxidant powder (GCA, Earth Supplied Products, Naples, Fla.), dissolved in the aqueous system. A 750 gram aliquot of this composition was dispersed into 200 grams of icosane (Permethyl 102-A, Presperse Corp., Somerset, N.J.) with 50 grams of sorbitan monooleate (Jeechem SMO, Jeen International Corp., Fairfield, N.J.) under high shear using a rotor-stator homogenizer (Silverson L4R, Silverson Machines, Inc., East Longmeadow, Mass.). The resulting thick cream was stable for at least weeks at 50° C. and was unaffected by freeze/thaw cycling.

Example 43

Foam Product Stabilized by Synergistic Succulent-Alginate

A 25 gram aliquot of a 1% aqueous solution of sodium alginate was combined with 5 grams of 30% cocamidopropyl betaine (Tego Betaine CK KB 5, Evonik Industries, AG., Essen, Germany) and 0.3 grams of coco-glucosides (Pureact Gluco C, Innospec, Littleton, Colo.) and stirred until these components were completely dissolved. To the resultant clear solution was added an additional 25 grams of 1% *Aloe* extract (100% Organic *Aloe Vera* Whole Leaf Powder 200X, Earth Supplied Products, Naples, Fla.), thus forming a clear, viscous, shear-thinning rheology product. The product thus formed was capable of being dispensed through a common personal care self-foamer (30 mm Natural Foamer w/ 3¼" Tube, Item ID: DP102, Container & Packaging Supply, Eagle, Id.). The foam formed upon dispensing was stabilized by the succulent-alginate rheological characteristics, and the foam thus formed showed improved stability and persistence compared to that formed by a comparable solution of the aqueous surfactants alone.

Example 44

Sprayable Cooling Composition

The product of Example 1 was sprayed onto a surface, for instance skin, as a fine mist. As the resulting adherent droplets evaporate, the surface was cooled. On skin, at an ambient temperature of 25° C. and relative humidity of 35%, application of 0.15 g of a mist comprising water alone was immediately cooling but evaporated in under a minute to dryness, after which the cooling sensation was rapidly lost. Under the same application conditions the product of Example 1 similarly provided rapid cooling, but the composition remained damp for several minutes and the cooling effect was prolonged. Without being bound to a particular interpretation, the immediate cooling provided by water or the exemplary product may be due to the liquid heat capacity, while the prolongation of cooling is due to evaporative cooling. As the product of Example 1 dried more slowly, the cooling effect was prolonged. In both cases presumably the net energy removed from the surface was the same, but the perception of cooling persisted longer for the slowly evaporating gel product.

Example 45

Sprayable Glove Coating Product

The product of Example 1 was modified by dispersing within it 5% wt each of slurries of microcapsules containing polydimethylsiloxane, shea (*vitellaria paradoxica*) nut oil, and a fragrance (all materials offered as ESP Vegabead encapsulates, Earth Supplied Product, Naples, Fla.). The exemplary product thus formed was applied to the inner surface of common flocked rubber washing gloves while the gloves were inverted, and dried under a warm air flow. The resulting treatment provided very noticeable improvement in the ease with which the gloves could be put on and removed, reduction in "rubbery" feel and the sensation of dampness due to perspiration, improved sensation of cushioning by the flocking, and improved skin feel and odor upon removing the gloves, with a strong reduction in rubber odor transfer to the skin accompanied by transfer of fragrance and skin emollients.

Example 46

Contractile Film

The product of Example 1 was applied to skin by spraying to form a uniform layer of 0.2 mm or more in thickness. As the water content of the film evaporated, the polysaccharide solution concentration increased to form a firm gel. As the gel dried further through evaporation, it developed tensile stress as the polymer network contracted through loss of water. The tension thus applied to the skin in the adherent conformal film had the result of tightening and firming the underlying skin.

Example 47

Gel Particles Containing Dispersed Gas

The product of Example 3 is reproduced, with the modification that the alginate solution is aerated to include gas bubbles, for instance by carbonation, such that droplets falling into the bath are buoyant and rise to the surface of the bath. The *Aloe* bath may be further modified by addition of lower density organic solvents such as methanol, ethanol, isopropanol, acetone or similarly water-soluble organic solvents. Without being bound to a particular interpretation, solvents that alter the density and/or surface tension of the bath may thereby alter the dynamics of droplet immersion and buoyancy of particles falling into the bath, permitting a longer contact time with the bath before surfacing. Such solvents may further affect the dynamics of precipitation of the polymers to promote entrapment of the gas phase within the particulate products thus formed.

Example 48

Cast Gel Containing Dispersed Material

The process of Example 23 may be modified by dispersing additional materials within the alginate phase such that the gel material thus formed contains inclusions. Suitable materials for including in the product include but are not limited to the following: emollient oil phases, water-insoluble clays and pigments, plant materials such as beneficial herbs, dried flowers, and plant fibers, poorly water-soluble or slowly dissolving materials such as benzoyl peroxide, and dispersed gases so as to create bubbles or a foam structure.

Example 49

Aqueous Gels Formed Using Dry Powdered Succulent

A 1% aqueous solution of alginate is introduced to a sample of dry powdered succulent extract, for instance *Aloe vera* powder, such that the exterior of the volume of alginate is coated by the powder. As the powder dissolves into the alginate solution, gelation occurs. The resulting gelled mass may be rinsed in water to remove excess or wetted *Aloe* powder that is not incorporated into the gel structure. The alginate solution may be introduced as droplets or poured as into a form. The *Aloe* powder may be in the form of a fluidized bed, particles suspended in a stream of air, a loose bed of powder, or may constitute a form with an embossed shape, to which the resulting gel structure will conform.

Example 50

Aqueous Gels Infused After Formation with Water Soluble Materials

Alginate gel materials formed by any of the methods described herein, for example the beads of Example 3, are immersed in a bath comprising an aqueous solution of a material to be loaded into the gel, for example, a 0.2% solution of sodium fluorescein, (Sigma-Aldrich, St. Louis, Mo.). The fluorescein dye enters the gel beads by diffusion, and is visibly retained in the beads when they are removed from the loading bath. *Aloe* has an extensive history of use as a moisturizer and skin benefit agent in cosmetics and has been further found to have additional useful properties, including antiseptic, antifungal, wound and burn healing, antiulcer, antitumor, antidiabetic, anti-inflammatory, immunostimulant, and laxative activities. The compositions of the present invention may retain such activity due to the *Aloe* or related plant components, and may in some cases enhance or inhibit these activities in specific embodiments.

Example 51

Partially Dehydrated Gel Material for Rehydration to a Suspending Rheological System A 1 kg quantity of the synergistic gel taught in Example 1 above was prepared. To this gel material was added 500 g of 95% ethanol (SDA 40B, Earth Supplied Products, LLC, Naples, Fla.), producing an inhomogeneous suspension of gelatinous granules, which could be separated from the remaining thin ethanolic liquor by straining through a mesh screen. The remaining gelatinous mass was pressed repeatedly in absorbent paper or cloth to further remove the ethanolic continuous phase until the resultant densified solid mass weighed 50 g. This mass was rubbed or crumbled to form a fluffy granular finished product. The resulting product, if added to water at a 5% level, rapidly rehydrated with stirring to form a shear-thinning clear fluid very similar in rheology to the original material of Example 1.

Example 52

Synergistic Gel System Formed from Alginate, Aloe vera, and Added Calcium

A 50 mL aliquot of 1% aqueous sodium alginate solution (Manucol® DH, FMC Health & Nutrition, Philadelphia, Pa.) was combined with a 40 mL aliquot of a 0.5% aqueous solution of Aloe vera powder (ESP Organic Aloe Vera 200X, Earth Supplied Products, LLC, Naples, Fla.) to form a product intermediate in viscosity to the two individual constituent solutions. To the resultant combined solution was gradually added 10 mL of an aqueous 0.1% calcium chloride solution while constantly stirring. When about 8 mL of the calcium solution had been added, the stirring solution viscosity increased noticeably. When the full 10 mL had been added, the solution was slightly more viscous than the material of Example 1, but performed well as a shear-thinning suspending agent.

Example 53

Reversible Sequestration to Produce a Triggerable Synergistic Rheological System A 50 mL aliquot of 1% aqueous sodium alginate solution (Manucol® DH, FMC Health & Nutrition, Philadelphia, Pa.) was combined with 50 mL of a solution comprising a 45 mL aliquot of a 0.5% aqueous solution of Aloe vera powder (ESP Organic Aloe Vera 200X, Earth Supplied Products, LLC, Naples, Fla.) combined with 5 mL of a 2% Disodium EDTA (Spectrum Laboratories, New Brunswick, N.J.). The resulting solution was intermediate in viscosity to the two alginate and Aloe vera solutions. To the resultant combined solution was gradually added approximately 1.5 mL of 10% citric acid (Earth Supplied Products, LLC, Naples, Fla.), reducing the pH to between 4 and 5. As the pH shifted below 5, the solution thickened rapidly. Without being bound to a particular understanding, the pH shift is believed to liberate calcium ions previously sequestered by EDTA to reform a system similar to that of Example 1.

Example 54

Dry Powder Rehydratable to form a Suspending Synergistic Gel Using Reversible Sequestration of Calcium Ions A dry powder comprising 30% Aloe vera solids, 30% disodium EDTA, and 35% alginate (Manucol DH, FMC Biopolymers, Philadelphia, Pa.) was compounded. A 1.0 g aliquot of the powder was wetted with 95% ethanol and added to 99 g stirring water to form a clear solution of about 30-40 cps viscosity. To this solution was added 3 mL of a 10% citric acid solution, sufficient to adjust the pH to approximately 4.5, at which point the solution rapidly thickened to form a >3000 cps viscosity solution similar to the product of Example 1.

Example 55

Dry Powder for Direct Hydration to Form an Aqueous Gel

A quantity of 90 g of sodium alginate (Manucol® DH, FMC Health & Nutrition, Philadelphia, Pa.) was blended with 5 g of Aloe vera powder (ESP Organic Aloe Vera 200X, Earth Supplied Products, LLC, Naples, Fla.) and 5 g of tricalcium citrate (Jungbunzlauer, Inc., Newton Center, Mass.). The resulting powdered composition could be directly added to stirring water or pre-wetted with ethanol, glycerin, or similar common wetting agents, or further modified by the addition of dispersant materials such as maltodextrins or other water-soluble materials to reduce clumping during addition. The product could be used effectively at 0.5%-1.0% to produce a highly shear thinning but strongly suspending gel. The wetted powder was stirred for 10-30 minutes to form a moderate viscosity (<1000 cps) clear solution. The solution thickened upon further standing overnight, and also thickened rapidly upon addition of 0.15% citric acid to form a >3000 cps strongly shear thinning final product.

Example 56

Suspending Gel System Incorporating Anionic Surfactant

A quantity of 85 g of sodium alginate (Manucol® DH, FMC Health & Nutrition, Philadelphia, Pa.) was blended with 5 g of Aloe vera powder (ESP Organic Aloe Vera 200X, Earth Supplied Products, Naples, Fla.) and 10 g of tricalcium citrate (Jungbunzlauer, Inc., Newton Center, Mass.). The powder was dispersed in 94 g water as in Example 55 above. To the resulting solution was added 6 g sodium lauryl sulfate 30% solution (Sulfochem™ SLS-K Surfactant, Lubrizol Corp., Wickliffe, Ohio). Upon acidification by addition of 0.15% citric acid, the composition rapidly thickened to a >3000 cps strongly shear thinning final product, with good foaming and cleaning properties. Without wishing to be bound by a particular interpretation, the product performance appears to be highly tolerant of hard water, perhaps due to intrinsically high calcium levels in the product as formed.

Example 57

Suspending Gel System Incorporating 0.1% Benzalkonium Chloride

A 20 mL aliquot of a solution was prepared, containing 0.625% Aloe (ESP Organic Aloe Vera 200X, Earth Supplied Products, Naples, Fla.) solids and 0.250% benzalkonium chloride (Spectrum Chemicals, New Brunswick, N.J.) in water. The 20 mL aliquot was gradually added to 30 mL of an aqueous solution containing 1% sodium alginate (Manucol® DH, FMC Health & Nutrition, Philadelphia, Pa.) and then adjusting to approximately pH 6 by addition of about 0.5 mL 10% citric acid solution (Earth Supplied Products, Naples, Fla.) to produce a viscous shear-thinning solution with properties comparable to those of the product of Example 1, except that the product formed with inclusion of benzalkonium chloride was substantially hazy, and visually nearly opaque. The product thus prepared contained 0.1% benzalkonium chloride, and may offer benefits as an antiseptic hand sanitizer, for example.

Example 58

Dry Powder Rehydratable to Produce a Surfactant-Tolerant Synergistic Rheological System A dry composition was compounded from 85% sodium alginate (Manucol® DH, FMC Health & Nutrition, Philadelphia, Pa.), 5% *Aloe vera* powder (ESP Organic *Aloe Vera* 200X, Earth Supplied Products, LLC, Naples, Fla.) and 10% tricalcium citrate (Jungbunzlauer, Inc., Newton Center, Mass.). A 1 g aliquot of the dry powder thus formed was wetted with 95% ethanol or similar and added to 69 g stirring water to form a hazy liquid system. To the resulting liquid system was added 30 g of a 30% aqueous solution of sodium lauryl sulfate (Sulfochem SLS-K, Lubrizol Corp., Wickliffe, Ohio). The viscosity of the resulting liquid was low, around 100 cps. To this product was added 3-5 mL of 10% citric acid solution to adjust the pH to around 5. As the pH dropped the liquid slowly clarified and became more viscous. After acidification, the final viscosity of the product was above 3000 cps and had good suspending, shear-thinning, and foaming qualities.

Example 59

Sprayable Aqueous Suspension Comprising a Synergistic Rheological System and an Organic Solvent To the aqueous gel system formed in Example 55 was added 5% content of propylene glycol Mono-n-propyl ether (DOWANOL™ PNP glycol ether, Dow Chemical Co., Midland, Mich.), to form a clear, viscous solution. The resulting solution was rheologically similar to the product of Example 1 and could be sprayed onto a vertical surface as a non-drip cleaning product, providing the combined benefits of the rheological system and the solvent.

Example 60

Sprayable Aqueous Suspension Comprising a Synergistic Rheological System and an Immiscible Dispersed Solvent A 1 g aliquot of the dry composition of Example 55 was dispersed in 78.5 g water and stirred to form a clear solution, but not acidified to develop viscosity. To this system was added 0.5 g Tween 20 (Ritabate 20, Rita Corp., Crystal Lake, Ill.) with stirring to dissolve. To the aqueous phase was added a second, organic phase comprising 20 g D/L limonene (Spectrum Chemicals, New Brunswick, N.J., with stirring to form a fine emulsion of the organic phase in the aqueous continuous phase. The product was acidified to pH 5 with 0.5 g 10% citric acid solution to develop viscosity. The resulting product provided a drip-resistant liquid that could readily be sprayed onto a vertical surface, for example to remove graffiti made with permanent marker. The product clung to the surface for localized application, and was easily wiped away.

Example 61

Sprayable Product for Skin and Hair Care

An aqueous gel system was formed by hydrating 1 g of the dry composition of Example 55 in 89.5 g of purified water. Into this system was dispersed 5 grams each, respectively, of encapsulated shea oil (ESP Vegabead Shea CS, Earth Supplied Products, Naples, Fla.) and encapsulated polydimethylsiloxane (ESP Vegabead Silicone CS, Earth Supplied Products, Naples, Fla.), and the resulting dispersion was acidified to pH 5.5 by addition of approximately 0.5 g 10% citric acid solution. The resulting product was stable to settling under freeze/thaw cycling and/or storage at 45 C for at least 6 months. The product was found to provide softness and moisturization to skin and hair and application to hair produces good slip and softness without tackiness. Notably, split-end damage treated with this composition was very effectively repaired upon application and brief drying. In a specific test of the repair efficacy, a population of 50 split-ends was treated with the recited product and 100% repair was observed upon initial treatment and after rinsing and re-drying the repair was maintained. The aqueous gel system did not itself produce robust repair of split ends, and surprisingly split-ends thus repaired showed increased durability compared to those repaired with a microcapsule suspension in water alone. Thus use of the aqueous gel system provided an unexpected strengthening of the repair. Without being bound to an interpretation, the formation of a non-dilutable gel upon drying such a product may add specific benefit to a split-end repair composition.

Example 62

Shaving Product Incorporating *Aloe*/Alginate Gel

An aqueous gel system was formed by hydrating 1 g of the dry composition of Example 58 in 90 g of purified water. Into this system was dispersed 5 grams each, respectively, of octyl-decyl glucoside (Surfapon AG-10, Tri-K Corp, Danville, N.J.) and cocamidopropyl betaine (JEETERIC CAB-LC, Jeen Corp., Fairfield, N.J.). The resulting solution was acidified to pH 5.5 with approximately 0.5 g 10% citric acid solution. The product thus formed was a clear gel that could be dispensed through a self-foamer pump to produce copious foam. The foam thus produced is useful as a shaving foam, and product was found to be lubricious and with soothing qualities. Surprisingly, during a use evaluation test of the recited product, occasional shaving nicks were observed to produce very minimal bleeding compared to when using ordinary shaving products.

What is claimed:
1. A composition, comprising:
a) a succulent extract, and
b) alginic acid and/or one or more salts thereof,
wherein the succulent extract is present in an amount in a range from 40 wt % to 80 wt % relative to the alginic acid and/or one or more salts thereof, both on a dry basis, wherein the composition has a viscosity that is higher than the viscosity of either component a) or b), and wherein chitosan is present in the composition in an amount of at most 15% by weight relative to the alginic acid and/or one or more salts thereof.

2. The composition of claim 1, further comprising a material capable of sequestering calcium ions.

3. The composition of claim 1, present as a solution or gel in water.

4. The composition of claim 3, further comprising a dispersed material suspended therein.

5. The composition of claim 3, further comprising one or more active materials selected from the group consisting of abrasives, antibacterial agents, deodorants, pigments and colorants, sunscreen actives, fragrance, pH indicators, living cells or organisms, seeds, spores, minerals, entrapped gases, surfactants, hair conditioning agents, bleaching agents, skin lightening agents, keratolytic agents, anti-inflammatory agents, emollients, antioxidants, vitamins, flavorants, proteins, nutritional supplements, medicaments, waxes, solvents, hormones, growth factors, immunomodulatory agents, chemotherapeutic agents, magnetic particles, semiconductors, photo-responsive materials, insect repellents, fertilizers, fracking proppants, defoliants, herbicides, and pesticides.

6. The composition of claim 1, wherein the composition is sprayable with a finger-pump, trigger-spray commercial dispenser.

7. The composition of claim 1, wherein the succulent extract is an extract of *Aloe vera*.

8. The composition of claim 1, wherein the succulent extract is an extract of a plant selected from the order Asparagales, family Asparagaceae, sub-family Agave.

9. The composition of claim 1, wherein the succulent extract is an extract of a plant selected from the order Caryophyllales, family Aizoaceae.

10. The composition of claim 1, wherein the succulent extract is an extract of a plant selected from the order Saxifragales, family Crassulaceae.

11. The composition of claim 1, which is in the form of a gel.

12. The composition of claim 1, which is in the form of a dry powder.

13. The composition of claim 1, which is pseudoplastic and/or thixotropic.

14. The composition of claim 1, further comprising particles, wherein the particles contain at least one payload material entrapped therein.

15. A method of preparing the composition of claim 1, comprising combining a) and b).

16. A method of treating skin, comprising applying the composition of claim 1 to the skin.

17. A method of treating a skin wound, comprising applying an effective amount of the composition of claim 1 to a skin wound.

18. A method of treating damaged skin, comprising applying an effective amount of the composition of claim 1 to a damaged skin.

* * * * *